US011262598B2

(12) United States Patent
Weeber et al.

(10) Patent No.: US 11,262,598 B2
(45) Date of Patent: Mar. 1, 2022

(54) DIFFRACTIVE LENSES AND RELATED INTRAOCULAR LENSES FOR PRESBYOPIA TREATMENT

(71) Applicant: AMO Groningen B.V., Groningen (NL)

(72) Inventors: Hendrik A. Weeber, Groningen (NL); Robert Rosen, Groningen (NL)

(73) Assignee: AMO Groningen, B.V., Groningen (NL)

( * ) Notice: Subject to any disclaimer, the term of this patent is extended or adjusted under 35 U.S.C. 154(b) by 132 days.

(21) Appl. No.: 16/020,928

(22) Filed: Jun. 27, 2018

(65) Prior Publication Data
US 2019/0004331 A1  Jan. 3, 2019

Related U.S. Application Data

(60) Provisional application No. 62/525,965, filed on Jun. 28, 2017.

(51) Int. Cl.
*G02C 7/04* (2006.01)
*G02C 7/02* (2006.01)
(Continued)

(52) U.S. Cl.
CPC ............ *G02C 7/044* (2013.01); *A61F 2/1618* (2013.01); *A61F 2/1654* (2013.01); *G02C 7/024* (2013.01); *G02C 7/042* (2013.01); *A61F 2/145* (2013.01); *A61F 2240/002* (2013.01); *G02C 2202/20* (2013.01)

(58) Field of Classification Search
CPC .... G02C 7/044; G02C 7/024; G02C 2202/20; G02C 7/042; A61F 2240/002; A61F 2/1654; A61F 2/1618; A61F 2/145
See application file for complete search history.

(56) References Cited

U.S. PATENT DOCUMENTS

| 3,367,734 A | 2/1968 | Karl et al. |
| 3,722,986 A | 3/1973 | Tagnon |

(Continued)

FOREIGN PATENT DOCUMENTS

| AU | 2005230194 B2 | 12/2010 |
| CA | 2501217 A1 | 4/2004 |

(Continued)

OTHER PUBLICATIONS

Morlock, R., et al., "Patient-Reported Spectacle Independence Questionnaire (PRSIQ): Development and Validation," American Journal of Ophthalmology, Jun. 2017, vol. 178, pp. 101-114.

(Continued)

*Primary Examiner* — Jack Dinh
(74) *Attorney, Agent, or Firm* — Johnson & Johnson Surgical Vision, Inc.

(57) ABSTRACT

Apparatuses, systems and methods for providing improved ophthalmic lenses, particularly intraocular lenses (IOLs), include features for reducing dysphotopsia effects, such as straylight, haloes and glare, in diffractive lenses. Exemplary ophthalmic lenses can include a diffractive profile that distributes light among a near focal length, a far focal length, and one or more intermediate focal length. The diffractive profile provides for minimized or zero step heights between one or more pairs of diffractive zones for reducing visual artifacts.

26 Claims, 12 Drawing Sheets

(51) Int. Cl.
　　　*A61F 2/16*　　　　(2006.01)
　　　*A61F 2/14*　　　　(2006.01)

(56) References Cited

U.S. PATENT DOCUMENTS

| | | | |
|---|---|---|---|
| 4,210,391 A | 7/1980 | Cohen | |
| 4,340,283 A | 7/1982 | Cohen | |
| 4,460,275 A | 7/1984 | Spriggs | |
| 4,504,892 A | 3/1985 | Zulfilar | |
| 4,504,982 A | 3/1985 | Burk | |
| 4,580,883 A | 4/1986 | Shinohara | |
| 4,606,626 A | 8/1986 | Shinohara | |
| 4,637,697 A | 1/1987 | Freeman | |
| 4,640,593 A | 2/1987 | Shinohara | |
| 4,641,934 A | 2/1987 | Freeman | |
| 4,642,112 A | 2/1987 | Freeman | |
| 4,655,565 A | 4/1987 | Freeman | |
| 4,710,193 A | 12/1987 | Volk | |
| 4,762,408 A | 8/1988 | Shinohara | |
| 4,778,462 A | 10/1988 | Grendahl | |
| 4,795,462 A | 1/1989 | Grendahl | |
| 4,798,608 A | 1/1989 | Grendahl | |
| 4,798,609 A | 1/1989 | Grendahl | |
| 4,856,234 A | 8/1989 | Goins | |
| 4,856,889 A | 8/1989 | Guilino et al. | |
| 4,881,804 A | 11/1989 | Cohen | |
| 4,881,805 A | 11/1989 | Cohen | |
| 4,898,461 A | 2/1990 | Portney | |
| 4,932,970 A | 6/1990 | Portney | |
| 4,936,666 A | 6/1990 | Futhey | |
| 4,957,506 A | 9/1990 | Mercier | |
| 4,978,211 A | 12/1990 | Cornu et al. | |
| 4,995,714 A | 2/1991 | Cohen | |
| 4,995,715 A | 2/1991 | Cohen | |
| 5,016,977 A | 5/1991 | Baude et al. | |
| 5,017,000 A | 5/1991 | Cohen | |
| 5,019,098 A | 5/1991 | Mercier | |
| 5,050,981 A | 9/1991 | Roffman | |
| 5,054,905 A | 10/1991 | Cohen | |
| 5,056,908 A | 10/1991 | Cohen | |
| 5,061,058 A | 10/1991 | Guilino et al. | |
| 5,066,301 A | 11/1991 | Wiley | |
| 5,076,684 A | 12/1991 | Simpson et al. | |
| 5,089,023 A | 2/1992 | Swanson | |
| 5,089,024 A | 2/1992 | Christie et al. | |
| 5,096,285 A | 3/1992 | Silberman | |
| 5,100,226 A | 3/1992 | Freeman | |
| 5,104,212 A | 4/1992 | Taboury et al. | |
| 5,112,351 A | 5/1992 | Christie et al. | |
| 5,114,220 A | 5/1992 | Baude et al. | |
| 5,116,111 A | 5/1992 | Simpson et al. | |
| 5,117,306 A | 5/1992 | Cohen | |
| 5,120,120 A | 6/1992 | Cohen | |
| 5,121,979 A | 6/1992 | Cohen | |
| 5,121,980 A | 6/1992 | Cohen | |
| 5,129,718 A | 7/1992 | Futhey et al. | |
| 5,144,483 A | 9/1992 | Cohen | |
| 5,148,205 A | 9/1992 | Guilino et al. | |
| 5,161,057 A | 11/1992 | Johnson | |
| 5,173,723 A | 12/1992 | Volk et al. | |
| 5,178,636 A | 1/1993 | Silberman | |
| 5,191,366 A | 3/1993 | Kashiwagi | |
| 5,220,359 A | 6/1993 | Roffman | |
| 5,225,858 A | 7/1993 | Portney | |
| 5,229,797 A | 7/1993 | Futhey et al. | |
| 5,236,970 A | 8/1993 | Christ et al. | |
| 5,257,132 A | 10/1993 | Ceglio et al. | |
| 5,260,727 A | 11/1993 | Oksman et al. | |
| 5,322,649 A | 6/1994 | Rheinish et al. | |
| 5,344,447 A | 9/1994 | Swanson | |
| 5,349,394 A | 9/1994 | Freeman et al. | |
| 5,349,471 A | 9/1994 | Morris et al. | |
| 5,381,190 A | 1/1995 | Rehse et al. | |
| 5,384,606 A | 1/1995 | Koch et al. | |
| 5,408,281 A | 4/1995 | Zhang | |
| 5,443,506 A | 8/1995 | Garabet | |
| 5,443,507 A | 8/1995 | Jacobi | |
| 5,444,106 A | 8/1995 | Zhou et al. | |
| 5,446,508 A | 8/1995 | Kitchen | |
| 5,448,312 A | 9/1995 | Roffman et al. | |
| 5,485,228 A | 1/1996 | Roffman et al. | |
| 5,581,405 A | 12/1996 | Meyers et al. | |
| 5,589,982 A | 12/1996 | Faklis et al. | |
| 5,629,800 A | 5/1997 | Hamblen | |
| 5,652,638 A | 7/1997 | Roffman et al. | |
| 5,674,284 A | 10/1997 | Chang et al. | |
| 5,682,223 A | 10/1997 | Menezes et al. | |
| 5,683,457 A | 11/1997 | Gupta et al. | |
| 5,684,560 A | 11/1997 | Roffman et al. | |
| 5,684,595 A | 11/1997 | Kato et al. | |
| 5,699,142 A | 12/1997 | Lee et al. | |
| 5,715,031 A | 2/1998 | Roffman et al. | |
| 5,715,091 A | 2/1998 | Meyers | |
| 5,724,258 A | 3/1998 | Roffman | |
| 5,728,156 A | 3/1998 | Gupta et al. | |
| 5,748,282 A | 5/1998 | Freeman | |
| 5,760,871 A | 6/1998 | Kosoburd et al. | |
| 5,777,719 A | 7/1998 | Williams et al. | |
| 5,796,462 A | 8/1998 | Roffman et al. | |
| 5,800,532 A | 9/1998 | Lieberman | |
| 5,805,260 A | 9/1998 | Roffman et al. | |
| 5,822,091 A | 10/1998 | Baker | |
| 5,838,496 A | 11/1998 | Maruyama et al. | |
| 5,847,802 A | 12/1998 | Menezes et al. | |
| 5,888,122 A | 3/1999 | Gupta et al. | |
| 5,895,422 A | 4/1999 | Hauber | |
| 5,895,610 A | 4/1999 | Chang et al. | |
| 5,929,969 A | 7/1999 | Roffman | |
| 5,968,094 A | 10/1999 | Werblin et al. | |
| 5,968,095 A | 10/1999 | Norrby | |
| 5,982,543 A | 11/1999 | Fiala | |
| 6,007,747 A | 12/1999 | Blake et al. | |
| 6,019,472 A | 2/2000 | Koester et al. | |
| 6,050,687 A | 4/2000 | Bille et al. | |
| 6,070,980 A | 6/2000 | Obara et al. | |
| 6,082,856 A | 7/2000 | Dunn et al. | |
| 6,086,204 A | 7/2000 | Magnante | |
| 6,089,711 A | 7/2000 | Blankenbecler et al. | |
| 6,095,651 A | 8/2000 | Williams et al. | |
| 6,120,148 A | 9/2000 | Fiala et al. | |
| 6,126,283 A | 10/2000 | Wen et al. | |
| 6,126,286 A | 10/2000 | Portney | |
| 6,139,145 A | 10/2000 | Israel | |
| 6,142,625 A | 11/2000 | Sawano et al. | |
| 6,145,987 A | 11/2000 | Baude et al. | |
| 6,154,323 A | 11/2000 | Kamo | |
| 6,199,986 B1 | 3/2001 | Williams et al. | |
| 6,210,005 B1 | 4/2001 | Portney | |
| 6,215,096 B1 | 4/2001 | Von Wallfeld et al. | |
| 6,224,211 B1 | 5/2001 | Gordon | |
| 6,231,603 B1 | 5/2001 | Lang et al. | |
| 6,270,220 B1 | 8/2001 | Keren | |
| 6,271,915 B1 | 8/2001 | Frey et al. | |
| 6,325,510 B1 | 12/2001 | Golub et al. | |
| 6,338,559 B1 | 1/2002 | Williams et al. | |
| 6,353,503 B1 | 3/2002 | Spitzer et al. | |
| 6,413,276 B1 | 7/2002 | Werblin | |
| 6,429,972 B1 | 8/2002 | Ota et al. | |
| 6,439,720 B1 | 8/2002 | Graves et al. | |
| 6,457,826 B1 | 10/2002 | Lett | |
| 6,462,874 B1 | 10/2002 | Soskind | |
| 6,464,355 B1 | 10/2002 | Gil | |
| 6,474,814 B1 | 11/2002 | Griffin | |
| 6,488,708 B2 | 12/2002 | Sarfarazi | |
| 6,491,721 B2 | 12/2002 | Freeman et al. | |
| 6,497,483 B2 | 12/2002 | Frey et al. | |
| 6,511,180 B2 | 1/2003 | Guirao et al. | |
| 6,520,638 B1 | 2/2003 | Roffman et al. | |
| 6,527,389 B2 | 3/2003 | Portney | |
| 6,533,416 B1 | 3/2003 | Fermigier et al. | |
| 6,536,899 B1 | 3/2003 | Fiala | |
| 6,537,317 B1 | 3/2003 | Steinert et al. | |
| 6,547,391 B2 | 4/2003 | Ross, III et al. | |
| 6,547,822 B1 | 4/2003 | Lang | |

(56) References Cited

U.S. PATENT DOCUMENTS

| | | |
|---|---|---|
| 6,554,425 B1 | 4/2003 | Roffman et al. |
| 6,554,859 B1 | 4/2003 | Lang et al. |
| 6,557,992 B1 | 5/2003 | Dwyer et al. |
| 6,576,012 B2 | 6/2003 | Lang |
| 6,582,076 B1 | 6/2003 | Roffman et al. |
| 6,585,375 B2 | 7/2003 | Donitzky et al. |
| 6,609,673 B1 | 8/2003 | Johnson |
| 6,609,793 B2 | 8/2003 | Norrby et al. |
| 6,616,275 B1 | 9/2003 | Dick et al. |
| 6,655,802 B2 | 12/2003 | Zimmermann et al. |
| 6,685,315 B1 | 2/2004 | De |
| 6,705,729 B2 | 3/2004 | Piers et al. |
| 6,709,103 B1 | 3/2004 | Roffman et al. |
| 6,755,524 B2 | 6/2004 | Rubinstein et al. |
| 6,791,754 B2 | 9/2004 | Ogawa |
| 6,802,605 B2 | 10/2004 | Cox et al. |
| 6,808,262 B2 | 10/2004 | Chapoy et al. |
| 6,818,158 B2 | 11/2004 | Pham et al. |
| 6,827,444 B2 | 12/2004 | Williams et al. |
| 6,830,332 B2 | 12/2004 | Piers et al. |
| 6,835,204 B1 | 12/2004 | Stork et al. |
| 6,846,326 B2 | 1/2005 | Zadno-Azizi et al. |
| 6,848,790 B1 | 2/2005 | Dick et al. |
| 6,851,803 B2 | 2/2005 | Wooley et al. |
| 6,884,261 B2 | 4/2005 | Zadno-Azizi et al. |
| 6,923,539 B2 | 8/2005 | Simpson et al. |
| 6,923,540 B2 | 8/2005 | Ye et al. |
| 6,951,391 B2 | 10/2005 | Morris et al. |
| 6,957,891 B2 | 10/2005 | Fiala |
| 6,972,032 B2 | 12/2005 | Aharoni et al. |
| 6,986,578 B2 | 1/2006 | Jones |
| 7,025,456 B2 | 4/2006 | Morris et al. |
| 7,036,931 B2 | 5/2006 | Lindacher et al. |
| 7,048,759 B2 | 5/2006 | Bogaert et al. |
| 7,048,760 B2 | 5/2006 | Cumming |
| 7,061,693 B2 | 6/2006 | Zalevsky |
| 7,073,906 B1 | 7/2006 | Portney |
| 7,093,938 B2 | 8/2006 | Morris et al. |
| 7,111,938 B2 | 9/2006 | Andino et al. |
| 7,137,702 B2 | 11/2006 | Piers et al. |
| 7,156,516 B2 | 1/2007 | Morris et al. |
| 7,159,983 B2 | 1/2007 | Menezes et al. |
| 7,188,949 B2 | 3/2007 | Bandhauer et al. |
| 7,198,640 B2 | 4/2007 | Nguyen |
| 7,217,375 B2 | 5/2007 | Lai |
| 7,221,513 B2 | 5/2007 | Cho et al. |
| 7,232,218 B2 | 6/2007 | Morris et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,377,641 B2 | 5/2008 | Piers et al. |
| 7,441,894 B2 | 10/2008 | Zhang et al. |
| 7,455,404 B2 | 11/2008 | Bandhauer et al. |
| 7,475,986 B2 | 1/2009 | Dai et al. |
| 7,481,532 B2 | 1/2009 | Hong et al. |
| 7,543,937 B2 | 6/2009 | Piers et al. |
| 7,572,007 B2 | 8/2009 | Simpson |
| 7,604,350 B2 | 10/2009 | Dursteler et al. |
| 7,615,073 B2 | 11/2009 | Deacon et al. |
| 7,654,667 B2 | 2/2010 | Blum et al. |
| 7,670,371 B2 | 3/2010 | Piers et al. |
| 7,677,725 B2 | 3/2010 | Piers et al. |
| 7,717,558 B2 | 5/2010 | Hong et al. |
| 7,753,521 B2 | 7/2010 | Wooley et al. |
| 7,871,162 B2 | 1/2011 | Weeber |
| 7,883,207 B2 | 2/2011 | Iyer et al. |
| 7,896,916 B2 | 3/2011 | Piers et al. |
| 7,922,326 B2 | 4/2011 | Bandhauer et al. |
| 7,984,990 B2 | 7/2011 | Bandhauer et al. |
| 7,998,198 B2 | 8/2011 | Angelopoulos et al. |
| 8,128,222 B2 | 3/2012 | Portney |
| 8,157,374 B2 | 4/2012 | Bandhauer et al. |
| 8,192,022 B2 | 6/2012 | Zalevsky |
| 8,197,063 B2 | 6/2012 | Iyer et al. |
| 8,216,307 B2 | 7/2012 | Schaper, Jr. |
| 8,231,219 B2 | 7/2012 | Weeber |
| 8,231,673 B2 | 7/2012 | Sacharoff et al. |
| 8,235,525 B2 | 8/2012 | Lesage et al. |
| 8,240,850 B2 | 8/2012 | Apter et al. |
| 8,262,728 B2 | 9/2012 | Zhang et al. |
| 8,292,953 B2 | 10/2012 | Weeber et al. |
| 8,382,281 B2 | 2/2013 | Weeber |
| 8,388,137 B2 | 3/2013 | Dreher et al. |
| 8,430,508 B2 | 4/2013 | Weeber |
| 8,444,267 B2 | 5/2013 | Weeber et al. |
| 8,480,228 B2 | 7/2013 | Weeber |
| 8,500,805 B2 | 8/2013 | Kobayashi et al. |
| 8,506,075 B2 | 8/2013 | Bandhauer et al. |
| 8,529,623 B2 | 9/2013 | Piers et al. |
| 8,556,416 B2 | 10/2013 | Lawu |
| 8,556,417 B2 | 10/2013 | Das et al. |
| 8,573,775 B2 | 11/2013 | Weeber |
| 8,619,362 B2 | 12/2013 | Portney |
| 8,636,796 B2 | 1/2014 | Houbrechts et al. |
| 8,652,205 B2 | 2/2014 | Hong et al. |
| 8,678,583 B2 | 3/2014 | Cohen |
| 8,709,079 B2 | 4/2014 | Zhang et al. |
| 8,734,511 B2 | 5/2014 | Weeber et al. |
| 8,740,978 B2 | 6/2014 | Weeber et al. |
| 8,747,466 B2 | 6/2014 | Weeber et al. |
| 8,755,117 B2 | 6/2014 | Kobayashi et al. |
| 8,771,348 B2 | 7/2014 | Zhao |
| 8,827,446 B2 | 9/2014 | Iyer et al. |
| 8,906,089 B2 | 12/2014 | Piers et al. |
| 9,069,185 B2 | 6/2015 | Zhao |
| 9,078,745 B2 | 7/2015 | Zhang et al. |
| 9,122,074 B2 | 9/2015 | Piers et al. |
| 9,164,201 B2 | 10/2015 | Fermigier et al. |
| 9,223,148 B2 | 12/2015 | Fiala et al. |
| 9,304,329 B2 | 4/2016 | Zhao |
| 9,310,624 B2 | 4/2016 | Argal et al. |
| 9,320,594 B2 | 4/2016 | Schwiegerling |
| 9,329,309 B2 | 5/2016 | Van |
| 9,335,563 B2 | 5/2016 | Weeber |
| 9,335,564 B2 | 5/2016 | Choi et al. |
| 9,370,416 B2 | 6/2016 | Argal et al. |
| 9,518,864 B2 | 12/2016 | Grossinger et al. |
| 9,563,070 B2 | 2/2017 | Ando et al. |
| 9,622,856 B2 | 4/2017 | Weeber et al. |
| 9,869,580 B2 | 1/2018 | Grossinger et al. |
| 9,925,041 B2 | 3/2018 | Gerlach et al. |
| 9,931,200 B2 | 4/2018 | Van et al. |
| 2001/0018612 A1 | 8/2001 | Carson et al. |
| 2002/0082690 A1 | 6/2002 | Sarbadhikari |
| 2002/0093701 A1 | 7/2002 | Zhang et al. |
| 2002/0105617 A1 | 8/2002 | Norrby et al. |
| 2002/0118337 A1 | 8/2002 | Perrott et al. |
| 2002/0122153 A1 | 9/2002 | Piers et al. |
| 2003/0014107 A1 | 1/2003 | Reynard |
| 2003/0063254 A1 | 4/2003 | Piers et al. |
| 2003/0076478 A1 | 4/2003 | Cox |
| 2003/0169491 A1 | 9/2003 | Bender et al. |
| 2003/0171808 A1 | 9/2003 | Phillips |
| 2004/0021824 A1 | 2/2004 | Ye et al. |
| 2004/0080710 A1 | 4/2004 | Wooley et al. |
| 2004/0085515 A1 | 5/2004 | Roffman et al. |
| 2004/0088050 A1 | 5/2004 | Norrby et al. |
| 2004/0106992 A1 | 6/2004 | Lang et al. |
| 2004/0111153 A1 | 6/2004 | Woods et al. |
| 2004/0138746 A1 | 7/2004 | Aharoni et al. |
| 2004/0150789 A1 | 8/2004 | Jones |
| 2004/0156014 A1 | 8/2004 | Piers et al. |
| 2004/0169820 A1 | 9/2004 | Dai et al. |
| 2004/0189981 A1 | 9/2004 | Ross et al. |
| 2004/0230299 A1 | 11/2004 | Simpson et al. |
| 2004/0246440 A1 | 12/2004 | Andino et al. |
| 2004/0252274 A1 | 12/2004 | Morris et al. |
| 2005/0057720 A1 | 3/2005 | Morris et al. |
| 2005/0096226 A1 | 5/2005 | Stock et al. |
| 2005/0099589 A1 | 5/2005 | Ishak |
| 2005/0128432 A1 | 6/2005 | Altmann |
| 2005/0203619 A1 | 9/2005 | Altmann |
| 2005/0259222 A1 | 11/2005 | Kelch et al. |

(56) References Cited

U.S. PATENT DOCUMENTS

| | | |
|---|---|---|
| 2005/0264757 A1 | 12/2005 | Morris et al. |
| 2005/0267575 A1 | 12/2005 | Nguyen et al. |
| 2006/0004446 A1 | 1/2006 | Aharoni et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 | 3/2006 | Blum et al. |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0139570 A1 | 6/2006 | Blum et al. |
| 2006/0176572 A1 | 8/2006 | Fiala |
| 2006/0238702 A1 | 10/2006 | Glick et al. |
| 2006/0244904 A1 | 11/2006 | Hong et al. |
| 2006/0244905 A1 | 11/2006 | Piers et al. |
| 2007/0002444 A1 | 1/2007 | Piers et al. |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0236769 A1 | 10/2007 | Zalevsky |
| 2007/0258143 A1 | 11/2007 | Portney |
| 2007/0268451 A1 | 11/2007 | Raghuprasad |
| 2007/0282438 A1 | 12/2007 | Hong et al. |
| 2008/0030677 A1 | 2/2008 | Simpson |
| 2008/0147185 A1 | 6/2008 | Hong et al. |
| 2008/0161913 A1 | 7/2008 | Brady et al. |
| 2008/0161914 A1 | 7/2008 | Brady et al. |
| 2008/0269891 A1 | 10/2008 | Hong et al. |
| 2008/0273169 A1 | 11/2008 | Blum et al. |
| 2008/0300679 A1 | 12/2008 | Altmann |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0240328 A1 | 9/2009 | Treushnikov et al. |
| 2009/0295295 A1 | 12/2009 | Shannon et al. |
| 2009/0323020 A1 | 12/2009 | Zhao et al. |
| 2010/0014049 A1 | 1/2010 | Bandhauer et al. |
| 2010/0016961 A1 | 1/2010 | Hong et al. |
| 2010/0057202 A1 | 3/2010 | Bogaert |
| 2010/0087921 A1 | 4/2010 | Simpson |
| 2010/0097569 A1 | 4/2010 | Weeber et al. |
| 2010/0100177 A1 | 4/2010 | Zhao |
| 2010/0131060 A1 | 5/2010 | Simpson et al. |
| 2010/0161048 A1 | 6/2010 | Schaper, Jr. |
| 2010/0161051 A1 | 6/2010 | Hong |
| 2010/0274233 A1 | 10/2010 | Dick et al. |
| 2010/0281021 A1 | 11/2010 | Weeber et al. |
| 2010/0312336 A1 | 12/2010 | Hong et al. |
| 2010/0321635 A1 | 12/2010 | Apter et al. |
| 2011/0022170 A1 | 1/2011 | Simpson et al. |
| 2011/0098811 A1 | 4/2011 | Hong et al. |
| 2011/0109874 A1 | 5/2011 | Piers et al. |
| 2011/0125261 A1 | 5/2011 | Portney |
| 2011/0149236 A1 | 6/2011 | Weeber |
| 2011/0166652 A1 | 7/2011 | Bogaert et al. |
| 2011/0267693 A1 | 11/2011 | Kobayashi et al. |
| 2011/0270596 A1 | 11/2011 | Weeber |
| 2011/0292335 A1 | 12/2011 | Schwiegerling |
| 2011/0313522 A1 | 12/2011 | Hayes |
| 2011/0313523 A1 | 12/2011 | Hayes |
| 2011/0313525 A1 | 12/2011 | Cumming |
| 2011/0317124 A1 | 12/2011 | Weeber et al. |
| 2011/0317126 A1 | 12/2011 | Weeber |
| 2012/0029630 A1 | 2/2012 | Piers et al. |
| 2012/0059464 A1 | 3/2012 | Zhao |
| 2012/0140166 A1 | 6/2012 | Zhao |
| 2012/0143326 A1 | 6/2012 | Canovas et al. |
| 2012/0154740 A1 | 6/2012 | Bradley et al. |
| 2012/0165932 A1 | 6/2012 | Argal et al. |
| 2012/0170121 A1 | 7/2012 | Okada et al. |
| 2012/0283825 A1 | 11/2012 | Houbrechts et al. |
| 2012/0320335 A1 | 12/2012 | Weeber et al. |
| 2012/0323321 A1 | 12/2012 | Simonov et al. |
| 2013/0035760 A1 | 2/2013 | Portney |
| 2013/0046381 A1 | 2/2013 | Zalevsky et al. |
| 2013/0060330 A1 | 3/2013 | Weeber et al. |
| 2013/0107202 A1 | 5/2013 | Liang |
| 2013/0201445 A1 | 8/2013 | Das et al. |
| 2014/0172088 A1 | 6/2014 | Carson et al. |
| 2015/0022775 A1 | 1/2015 | Ando et al. |
| 2015/0029460 A1 | 1/2015 | Bradley et al. |
| 2015/0094807 A1 | 4/2015 | Piers et al. |
| 2015/0359625 A1 | 12/2015 | Argal |
| 2016/0216535 A1 | 7/2016 | Zhao |
| 2016/0220350 A1 | 8/2016 | Gerlach |
| 2016/0220352 A1 | 8/2016 | Choi et al. |
| 2016/0320633 A1 | 11/2016 | Weeber |
| 2016/0334640 A1 | 11/2016 | De, Jr. et al. |
| 2016/0341978 A1 | 11/2016 | Schwiegerling |
| 2017/0172088 A1 | 6/2017 | May |
| 2017/0209259 A1 | 7/2017 | Choi et al. |
| 2017/0216020 A1 | 8/2017 | Weeber et al. |
| 2017/0219846 A1 | 8/2017 | Ando |
| 2017/0227789 A1 | 8/2017 | Ando et al. |
| 2017/0239038 A1 | 8/2017 | Choi et al. |
| 2017/0245985 A1 | 8/2017 | Canovas et al. |
| 2017/0245986 A1 | 8/2017 | Canovas et al. |
| 2017/0245987 A1 | 8/2017 | Canovas et al. |
| 2017/0252151 A1 | 9/2017 | Mackool |
| 2018/0092739 A1 | 4/2018 | Pagnoulle et al. |
| 2018/0132996 A1 | 5/2018 | Tiwari et al. |
| 2018/0147050 A1 | 5/2018 | Choi et al. |
| 2018/0147052 A1 | 5/2018 | Hong et al. |
| 2018/0275428 A1 | 9/2018 | Ando |
| 2018/0373060 A1 | 12/2018 | Knox et al. |
| 2019/0004335 A1 | 1/2019 | Hendrik et al. |
| 2019/0224000 A1 | 7/2019 | Choi et al. |
| 2019/0254810 A1 | 8/2019 | Tiwari et al. |
| 2019/0307557 A1 | 10/2019 | De Carvalho et al. |
| 2019/0314148 A1 | 10/2019 | Liu |
| 2020/0038172 A1 | 2/2020 | Hussain et al. |

FOREIGN PATENT DOCUMENTS

| | | |
|---|---|---|
| CA | 2507659 A1 | 6/2004 |
| CA | 2590085 A1 | 6/2006 |
| CN | 1951340 A | 4/2007 |
| CN | 101181171 B | 4/2011 |
| CN | 102665611 A | 9/2012 |
| DE | 69715830 T2 | 8/2003 |
| EP | 335731 A2 | 10/1989 |
| EP | 342895 A2 | 11/1989 |
| EP | 0343067 A1 | 11/1989 |
| EP | 355230 A2 | 2/1990 |
| EP | 0369561 A2 | 5/1990 |
| EP | 375291 A2 | 6/1990 |
| EP | 412751 A2 | 2/1991 |
| EP | 0457553 A2 | 11/1991 |
| EP | 470811 A2 | 2/1992 |
| EP | 0537643 A1 | 4/1993 |
| EP | 605841 A1 | 7/1994 |
| EP | 0316162 B1 | 10/1995 |
| EP | 355230 B1 | 10/1995 |
| EP | 681198 A1 | 11/1995 |
| EP | 0537643 B1 | 3/1997 |
| EP | 0926531 A1 | 6/1999 |
| EP | 949529 A2 | 10/1999 |
| EP | 1376203 A2 | 1/2004 |
| EP | 1424049 A1 | 6/2004 |
| EP | 1862148 A1 | 12/2007 |
| EP | 1310267 B1 | 1/2008 |
| EP | 1891912 A1 | 2/2008 |
| EP | 2043558 A2 | 4/2009 |
| EP | 2045648 A1 | 4/2009 |
| EP | 1402308 B1 | 5/2009 |
| EP | 1424049 B1 | 6/2009 |
| EP | 2103279 A1 | 9/2009 |

(56) References Cited

FOREIGN PATENT DOCUMENTS

| | | |
|---|---|---|
| EP | 2113226 A1 | 11/2009 |
| EP | 2365379 A1 | 9/2011 |
| EP | 2377493 A1 | 10/2011 |
| EP | 2378319 A1 | 10/2011 |
| EP | 2290411 B1 | 5/2012 |
| EP | 2363097 B1 | 9/2012 |
| EP | 2812882 A1 | 12/2014 |
| EP | 2813881 A1 | 12/2014 |
| EP | 2349093 B1 | 10/2015 |
| EP | 3150170 B1 | 12/2017 |
| EP | 2527908 B1 | 3/2019 |
| IT | 1215851 B | 2/1990 |
| JP | 1154119 A | 6/1989 |
| JP | 2028615 A | 1/1990 |
| JP | 2079815 A | 3/1990 |
| JP | 2137814 A | 5/1990 |
| JP | 2249631 A | 10/1990 |
| JP | 3011315 A2 | 1/1991 |
| JP | 2000511299 A | 8/2000 |
| JP | 2003532157 A | 10/2003 |
| JP | 2010158315 A | 7/2010 |
| JP | 2013101323 A | 5/2013 |
| KR | 101154066 B1 | 6/2012 |
| RU | 2011154235 A | 7/2013 |
| RU | 2011154238 A | 7/2013 |
| WO | 9002963 A1 | 3/1990 |
| WO | 9222264 A1 | 12/1992 |
| WO | 9303409 A1 | 2/1993 |
| WO | 9413225 A1 | 6/1994 |
| WO | 9417435 A1 | 8/1994 |
| WO | 9724639 A1 | 7/1997 |
| WO | 9744689 A1 | 11/1997 |
| WO | 9831299 A2 | 7/1998 |
| WO | 9907309 A1 | 2/1999 |
| WO | 9923526 A1 | 5/1999 |
| WO | 0019906 A1 | 4/2000 |
| WO | 0076426 A2 | 12/2000 |
| WO | 0121061 A1 | 3/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 0234158 A2 | 5/2002 |
| WO | 02084381 A2 | 10/2002 |
| WO | 02088830 A1 | 11/2002 |
| WO | 03009053 A1 | 1/2003 |
| WO | 2004013680 A1 | 2/2004 |
| WO | 2004034129 A1 | 4/2004 |
| WO | 2004049979 A1 | 6/2004 |
| WO | 2004090611 A2 | 10/2004 |
| WO | 2004096014 A2 | 11/2004 |
| WO | 2004113959 A2 | 12/2004 |
| WO | 05019906 A1 | 3/2005 |
| WO | 06025726 A1 | 3/2006 |
| WO | 2006047698 A1 | 5/2006 |
| WO | 06060477 A2 | 6/2006 |
| WO | 2006060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008150982 A1 | 12/2008 |
| WO | 2009017403 A1 | 2/2009 |
| WO | 2009027438 A2 | 3/2009 |
| WO | 2009043985 A1 | 4/2009 |
| WO | 2009058755 A1 | 5/2009 |
| WO | 2009076670 A1 | 6/2009 |
| WO | 2009130610 A2 | 10/2009 |
| WO | 2009148454 A1 | 12/2009 |
| WO | 2010046356 A1 | 4/2010 |
| WO | 2010054255 A1 | 5/2010 |
| WO | 2010059764 A1 | 5/2010 |
| WO | 2010079528 A1 | 7/2010 |
| WO | 2010093975 A2 | 8/2010 |
| WO | 2010100523 A1 | 9/2010 |
| WO | 2010104530 A1 | 9/2010 |
| WO | 2010144315 A1 | 12/2010 |
| WO | 2011024125 A1 | 3/2011 |
| WO | 2011055228 A2 | 5/2011 |
| WO | 2011075641 A2 | 6/2011 |
| WO | 2011075668 A1 | 6/2011 |
| WO | 2012004746 A2 | 1/2012 |
| WO | 2012031211 A1 | 3/2012 |
| WO | 2012070313 A1 | 5/2012 |
| WO | 2012078763 A1 | 6/2012 |
| WO | 2012085917 A1 | 6/2012 |
| WO | 2012122411 A1 | 9/2012 |
| WO | 2012140389 A1 | 10/2012 |
| WO | 2013018379 A1 | 2/2013 |
| WO | 2013028992 A1 | 2/2013 |
| WO | 2013093916 A1 | 6/2013 |
| WO | 2013114209 A2 | 8/2013 |
| WO | 2013116133 A1 | 8/2013 |
| WO | 2013118177 A1 | 8/2013 |
| WO | 2013118499 A1 | 8/2013 |
| WO | 2014008343 A1 | 1/2014 |
| WO | 2014033543 A2 | 3/2014 |
| WO | 2014091528 A1 | 6/2014 |
| WO | 2014111831 A1 | 7/2014 |
| WO | 2014189049 A1 | 11/2014 |
| WO | 2017137841 A1 | 8/2017 |
| WO | 2017149403 A1 | 9/2017 |
| WO | 2018093873 A1 | 5/2018 |
| WO | 2018150236 A1 | 8/2018 |
| WO | 2019130030 A1 | 7/2019 |
| WO | 2020115104 A1 | 6/2020 |

OTHER PUBLICATIONS

Seitz B., et al., "Corneal Topography," Current Opinion in Ophthalmolgy, 1997, vol. 8 (4), pp. 8-24.
Siedlecki D., et al., "Radial Gradient index Intraocular Lens: a Theoretical Model," Journal of Modem Optics, Feb. 20-Mar. 10, 2008, vol. 55 (4-5), pp. 639-647.
Smith G. et al., "The spherical aberration of the crystalline lens of the human eye," Vision Res., 2001, 41 (2), 235-243.
Smith Kinney, "Sensitivity of the eye to spectral radiation at scotopic and mesopic intensity levels," Journal of the Optical Society of America, 1955, 45 (7), 507-514.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Thibos L. N. et al., "The chromatic eye: a new reduced-eye model of ocular chromatic aberration in humans," Applied Optics, 1992, 31 (19), 3594-3600.
Thibos L. N. et al., "Theork and measurement of ocular chromatic aberration," Vision Res, 1988, 30 (1), 33-49.
Townsley, "New Knowledge of the corneal contour," Contacto, 1970, pp. 38-43.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Verriest G., "The Spectral Curve of Relative Luminous Efficiency in Different Age Groups of Aphakic Eyes," Mod Probl Ophthalmol., 1974, 13, 314-317.
Villegas E.A., et al., "Correlation between Optical and Psychophy, Sical Parameters as a Function of Defocus," Optometry and Vision Science, Jan. 1, 2002, vol. 79 (1), pp. 60-67.
Wang J.Y., et al., "Wave-Front Interpretation With Zernike Polynomials," Applied Optics, 1980, vol. 19 (9), pp. 1510-1518.
Albert D.M., "(Book Review) Intraocular Lenses: Evolution, Designs, Complications, and Pathology, by David Apple at al.," Archieves of Opthalmology, 1990, vol. 108, p. 650.
Alfonso J.F., et al., "Prospective Study of the Acri.LISA Bifocal Intraocular Lens," Journal of Cataract Refractive Surgery, Nov. 2007, vol. 33 (11), pp. 1930-1935.

(56) References Cited

OTHER PUBLICATIONS

Alvarez S. L. et al., "Spectral threshold: measurement and clinical applications," British Journal of Ophthalmology, 1983, 67, 504-507.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Artal P., et al., "Contributions of the Cornea and the Lens to the Aberrations of the Human Eye," Optics Letters, 1998, vol. 23 (21), pp. 1713-1715.
Atchinson D.A., "Design of Aspheric Intraocular Lens," Ophthamic & Physiological Optics, 1991, vol. 11 (2), pp. 137-146.
Atchinson D.A., et al., "Optical Design of Intraocular Lenses. II. Off-Axis performance," Optometry & Vision Science, 1989, vol. 66 (9), pp. 579-590.
Atchinson D.A., et al., "Third-Order Aberrations of Pseudophakic Eyes," Ophthalmic and Physiological Optics , 1989, vol. 9, pp. 205-211.
Atchinson D.A., "Optical Design of Intraocular Lenses. 1. On-Axis Performance," American Academy of Optometry, 1989, vol. 66 (8), pp. 492-506.
Atchinson D.A., "Optical design of intraocular lenses III. On-Axis Performance in the Presence of Lens Displacement," American Academy of Optometry, 1989, vol. 66 (10), pp. 671-681.
Atchinson, "Refractive errors induced by displacement of intraocular lenses within the pseudophakic eye," Optometry & Vision Science, 1989, 66 (3), 146-152.
Bonnet R., et al, "New Method of Topographical Ophthalmometry—Its Theoretical and Clinical Applications," American Journal of Optometry, 1962, vol. 39 (5), pp. 227-251.
Bradley A. et al., "Achromatizing the Human Eye" Optometry & Vision Science, 1991, vol. 68 (8), pp. 608-616.
Buralli D.A., et al, "Optical Performance of Holographic Kinoforms," Applied Optics, Mar. 1989, vol. 28 (5), pp. 976-983.
Canovas C., et al., "Hybrid Adaptive-Optics Visual Simulator," Optical Letters, Jan. 15, 2010, vol. 35 (2), pp. 196-198.
Cohen A.L., "Diffractive Bifocal Lens Design," Optometry and Vision Science, Jun. 1993, vol. 70 (6), pp. 461-468.
Cohen A.L., "Practical Design of a Bifocal Hologram Contact Lens or Intraocular Lens," Applied Optics, Jul. 1, 1992, vol. 31 (19), pp. 3750-3754.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Dwyer W. O. et al., "Racial Differences in Color Vision: Do They Exist", American Journal of Optometry & Physiological Optics, 1975, 52, 224-229.
El Hage S.G., et al., "Contribution of the Crystalline Lens to the Spherical Aberration of the Eye," 1973, vol. 63 (2), pp. 205-211.
Futhey J.A., "Diffractive Bifocal Intraocular Lens," SPIE, 1989, vol. 1052, pp. 142-148.
Geun Y., et al., "Visual Performance after Correcting the Monochromatic and Chromatic Aberrations of the Eye," Journal of the Optical Society of America, 2002, vol. 19 (2), pp. 266-275.
Glasser A. et al., "Presbyopia and the optical changes in the human crystalline lens with age," Vision Res, 1998, 38 (2), 209-229.
Greivenkamp J.E., et al., "Visual Acuity Modeling Using Optical Raytracing of Schematic Eyes," American Journal of Ophthalmology, 1995, vol. 120 (2), pp. 227-240.
Griswold Scott et al., "Scotopic Spectral Sensitivity of Phakic and Aphakic Observers Extending into the Near Ultraviolet," Vision res, 1992, 32 (9), 1739-1743.

Guirao A., et al., "Corneal Wave Aberration from Videokeratography: Accuracy and Limitations of the Procedure," Journal of the Optical Society of America, 2000, vol. 17 (6), pp. 955-965.
IOVS, 1999, 40 (4), S535.
Kiely et al., "The mean shape of the human cornea," Optica ACTA, 1982, 29 (8), 1027-1040.
Kokoschka S., et al., "Influence of Field Size on the Spectral Sensitivity of the Eye in the Photopic and Mesopic Range," American Journal of Optometry and Physiological Optics, 1985, vol. 62 (2), pp. 119-126.
Liang J., et al, "Objective Measurement of Wave Aberrations of the Human Eye With the Use of a Hartmann-Shack Wave-Front Sensor," Journal of the Optical Society of America, 1994, vol. 11 (7), pp. 1949-1957.
Lindsay R., et al., "Descriptors of Corneal Shape," Optometry and Vision Science, 1998, vol. 75 (2), pp. 156-158.
Liou H.L., et al., "Anatomically Accurate, Finite Model Eye for Optical Modeling," Journal of Optical Society of America, Aug. 1997, vol. 14 (8), pp. 1684-1695.
Lotmar, "Theoretical eye model with aspherics," Journal of the Optical Society of America, 1971, 61 (11), 1522-1529.
Malacara D., et al., "Wavefront Fitting With Discrete Orthogonal Polynomials in a Unit Radius Circle," Optical Engineering, 1990, vol. 29 (6), pp. 672-675.
Mandell R.B., et al., "Mathematical Model of the Corneal Contour," 1965, School of Optometry, University of California, Berkeley, pp. 183-197.
Marcos S., et al., "A New Approach to the Study of Ocular Chromatic Aberrations," Vision Research, 1999, vol. 39 (26), pp. 4309-4323.
Marsack J.D., et al., "Metrics of Optical Quality Derived from Wave Aberrations Predict Visual Performance," Journal of Vision, Apr. 2004, vol. 4 (4), pp. 322-328.
Monsoriu J.A., et al., "Devil's Lenses," Optics Express, Oct. 17, 2007, vol. 15 (21), p. 13858-13864.
Mordi J.A., et al., "Influence of Age of Chromatic Aberration of the Human Eye," American Journal of Optometry & Physiological Optics, 1985, vol. 62 (12), pp. 864-869.
Navarro R., et al., "Accommodation-Dependent Model of the Human Eye with Aspherics," Journal of the Optical Society of America, Aug. 1985, vol. 2 (8), pp. 1273-1281.
Norrby S., et al., "Model Eyes for Evaluation of Intraocular Lenses," Applied Optics, Sep. 7, 2007, vol. 46 (26), pp. 6595-6605.
"Optical Design," Military Standardization Handbook, 1962, Chapter 4, U.S. Department of Defense MIL-HDBK-141, 4-1-4-19.
Oshika T., et al., "Changes in Corneal Wavefront Aberrations with Aging," Investigative Ophthalmology & Visual Science, 1999, vol. 40 (7), pp. 1351-1355.
Patel S., et al., "Shape and Radius of Posterior Corneal Surface," Refractive and Corneal Surgery, 1993, vol. 9 (3), pp. 173-181.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Said et al., "The Variation with Age of the Spectral Transmissivity of the Living Human Crystalline Lens," Gerontologia, 1959, 213-231.
Schwiegerling et al., "Representation of videokeratoscopic height data with Zernike polynomials," Journal of the Optical Society of America, 1995, 12 (10), 2105-2113.
International Search Report and written opinion for Application No. PCT/EP2018/066780, dated Oct. 1, 2018, 14 pages.
Castignoles F., et al., "Comparison of the Efficiency, MTF and Chromatic Properties of Four Diffractive Bifocal Intraocular Lens Designs, " Optics Express, Mar. 2010, vol. 18 (5), pp. 5245-5256.
Sokolowski M., et al. "Hybrid Heptafocal Intraocular Lenses," Optica Applicata, Dec. 2015, vol. 45 (3), pp. 285-298.
Guillon M., et al., "Corneal Topography: A Clinical Model," Ophthalmic & Physiological Optics, 1986, vol. 6 (1), pp. 47-56.
Smith G., et al., "The spherical aberration of intra-ocular lenses," Department of Optometry, 1988, vol. 8 (3), pp. 287-294.

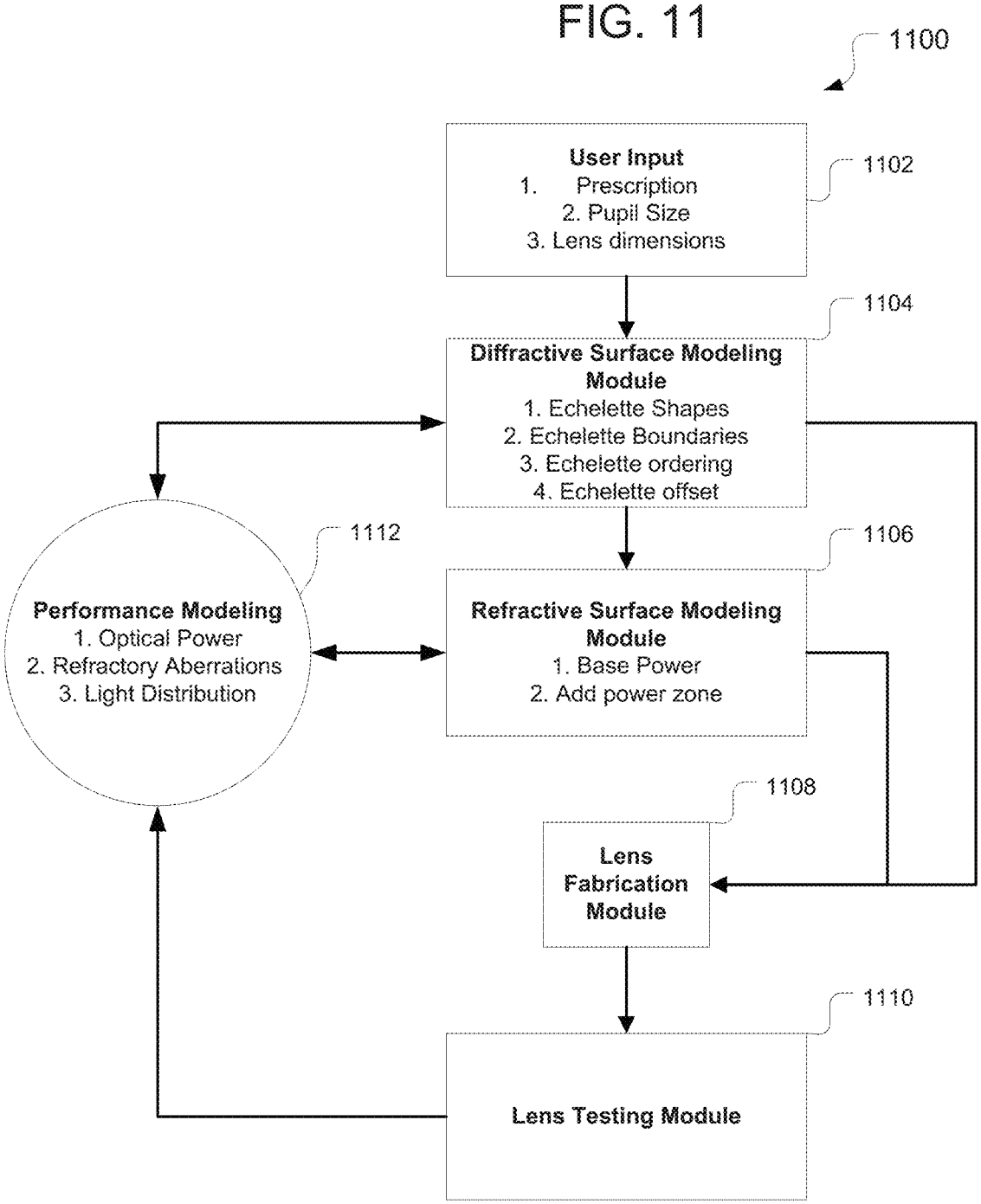

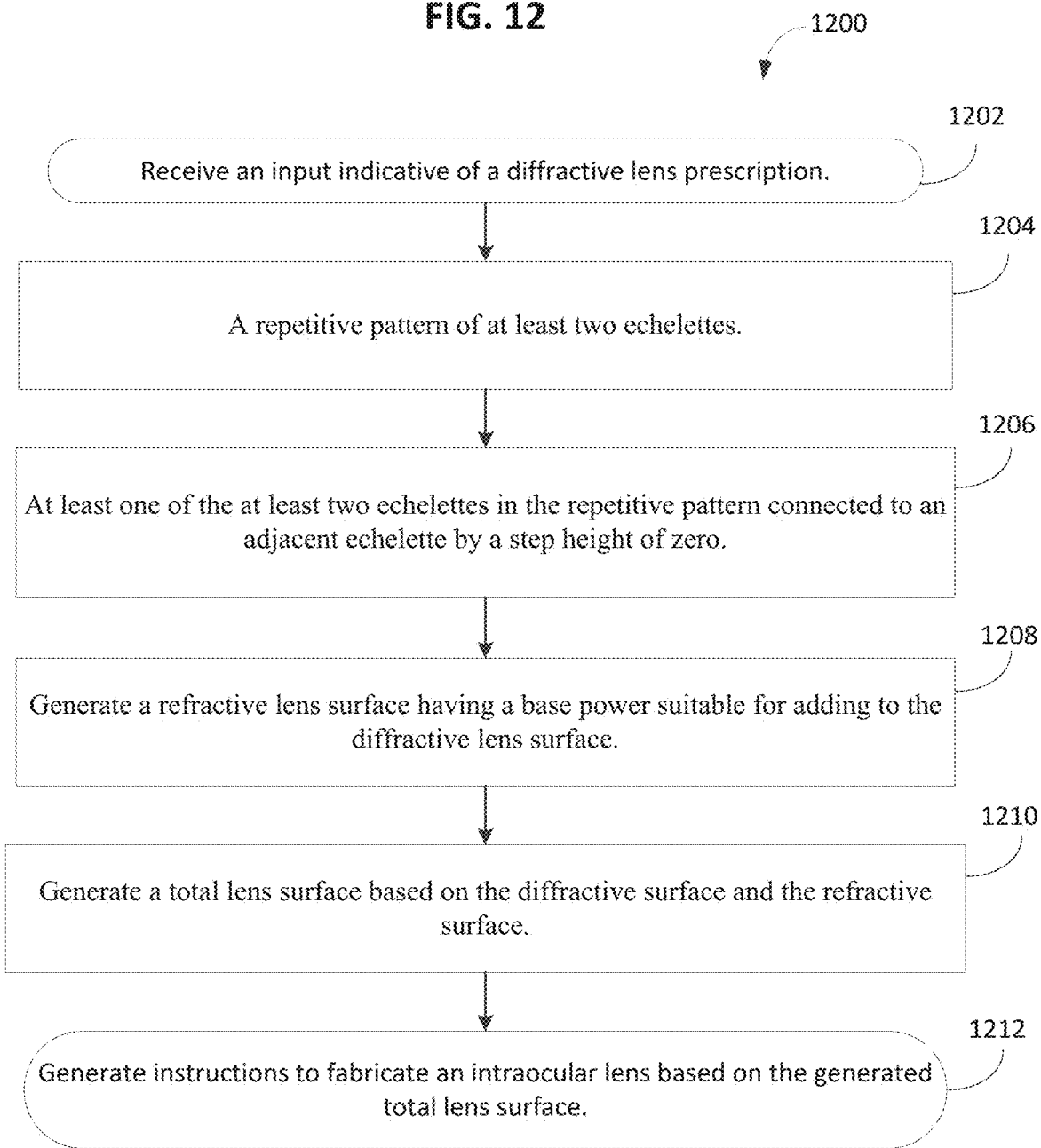

DIFFRACTIVE LENSES AND RELATED INTRAOCULAR LENSES FOR PRESBYOPIA TREATMENT

CROSS-REFERENCE AND RELATED APPLICATIONS

This application claims priority to, and the benefit of, under U.S.C. § 119(e) of U.S. Provisional Appl. No. 62/525,965, filed on Jun. 28, 2017, which is incorporated herein by reference in its entirety.

BACKGROUND

Embodiments of the present disclosure relate generally to diffractive ophthalmic lenses, and particular embodiments provide methods, devices, and systems for mitigating or treating vision conditions such as presbyopia, often by determining a desired multifocal power profile and selecting a geometry of the diffractive profile that results in a diffractive multifocal lens shape according to the desired power profile and to various parameters of the patient's eye. Embodiments also relate to vision treatment techniques and in particular embodiments, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL".

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive zones. When used for ophthalmic lenses these diffractive zones are typically annular lens zones, or echelettes, spaced about the optical axis of the lens. Each echelette may be defined by an optical zone, a transition zone between the optical zone and an optical zone of an adjacent echelette, and echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different powers. Together, these echelettes form a diffractive profile.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens. The lenses may be in the form of a contact lens, most commonly a bifocal contact lens, or in any other form mentioned herein.

Multifocal (e.g. diffractive) intraocular lenses (IOLs) are intended to provide a patient with improved vision at different distances, such as near, intermediate and far. The near vision may generally correspond to vision provided when objects are at a distance of equal or less than 1.5 feet from a subject eye. Intermediate vision may generally correspond to vision for objects at a distance between about 1.5 feet and about 5-6 feet from a subject eye. Far vision may generally correspond to vision for objects at any distance greater than about 5-6 feet from a subject eye. Such characterizations of near, intermediate, and far vision correspond to those addressed in Morlock R, Wirth R J, Tally S R, Garufis C, Heichel C W D, Patient-Reported Spectacle Independence Questionnaire (PRSIQ): Development and Validation. Am J Ophthalmology 2017; 178:101-114.

Since multifocal IOLs provide multiple focal lengths, the focused image on the retina originating from the focal length that corresponds to the particular viewing distance is overlapping with unfocused images originating from the other focal lengths. This can create visual artifacts for the patient. Also, the transitions between echelettes in a diffractive multifocal may cause glare, halo, or similar visual artifacts; and the severity of said artifacts may increase with an increased number of echelettes. Furthermore, conventional approaches typically provide for near and far vision, but achieve unsatisfactory visual performance at intermediate distances. Relatedly, increasing the number of focal lengths in an IOL can exacerbate the aforementioned visual artifacts. Therefore, multifocal conventional ophthalmic approaches may fail to adequately improve visual performance at intermediate distances.

BRIEF SUMMARY

Embodiments herein described include IOLs with a first surface and a second surface disposed about an optical axis, and a diffractive profile imposed on one of the first surface or the second surface. The diffractive profile includes a repetitive pattern of at least two echelettes. At least one of the at least two diffractive echelettes in the repetitive pattern is connected to an adjacent echellete by a step height of zero. The zero-step-height transition between at least one adjacent pair of diffractive echelettes is effective to reduce optical aberrations for a user, particularly straylight at the far vision.

Embodiments herein described also include multifocal ophthalmic lenses that have diffractive echelettes directing light to multiple focal lengths in ascending proportions, such that the least light is directed to the near focal length and/or such that the most light is directed to the far focal length. In some cases, at least 50% of the light that passes through the lens can be directed toward the far focal length; and no more than 20% of the light that passes through the lens can be directed toward the near focal length. One or more intermediate focal lengths may be provided.

Embodiments herein described also include ophthalmic lenses that have an optical surface disposed about an optical axis. A diffractive profile is imposed on the optical surface. The diffractive profile includes a set of at least two echelettes, with at least one of the at least two echelettes of the set being connected to an adjacent echelette with a step height of zero, and the set is repeated on the optical surface.

Embodiments herein described also include manufacturing systems for making an ophthalmic lens. Such manufacturing system can include an input that accepts an ophthalmic lens prescription for a patient eye. A module can generate a diffractive profile including a repetitive pattern of at least two echelettes, and at least one of the echelettes in the repetitive pattern is connected to an adjacent echelette by a step height of zero. A manufacturing assembly may fabricate the ophthalmic lens based on the diffractive profile. A manufacturing system may also include an input that accepts an ophthalmic lens prescription for a patient eye. A module can generate a diffractive profile configured to cause a distribution of light among at least three focal lengths including a near focal length, an intermediate focal length, and a far focal length, such that, a first portion of the distribution is directed to the near focal length, a second portion of the distribution is directed to the far focal length, and a third portion of the distribution is directed to the intermediate focal length, the first portion being less than the second portion and less than the third portion. A manufacturing assembly may fabricate the ophthalmic lens based on the diffractive profile.

Embodiments herein described also include methods of designing an intraocular lens. Such methods can include defining a diffractive profile and generating a diffractive lens surface based on the diffractive profile. The diffractive profile can include a repetitive pattern of at least two echelettes, and at least one of the at least two echelettes in the repetitive pattern is connected to an adjacent echelette by a step height of zero. The diffractive profile may also be configured such that a first portion of the distribution is directed to the near focal length, a second portion of the distribution is directed to the far focal length, and a third portion of the distribution is directed to the intermediate focal length, the first portion being less than the second portion and less than the third portion.

BRIEF DESCRIPTION OF THE DRAWINGS

FIG. 11 is a simplified block diagram illustrating a system for generating a diffractive lens surface, in accordance with embodiments;

FIG. 12 illustrates an example process for generating a diffractive lens surface; and FIG. 13 illustrates an example computing environment for facilitating the systems and processes of FIGS. 11 and 12.

DETAILED DESCRIPTION

Contemporary Lens Shapes and Diffractive Profiles

FIGS. 1A, 1B, 2A, and 2B illustrate multifocal IOL lens geometries, aspects of which are described in U.S. Patent Publication No. 2014-0168602 A1, which is hereby incorporated by reference in its entirety.

Figure 1A:
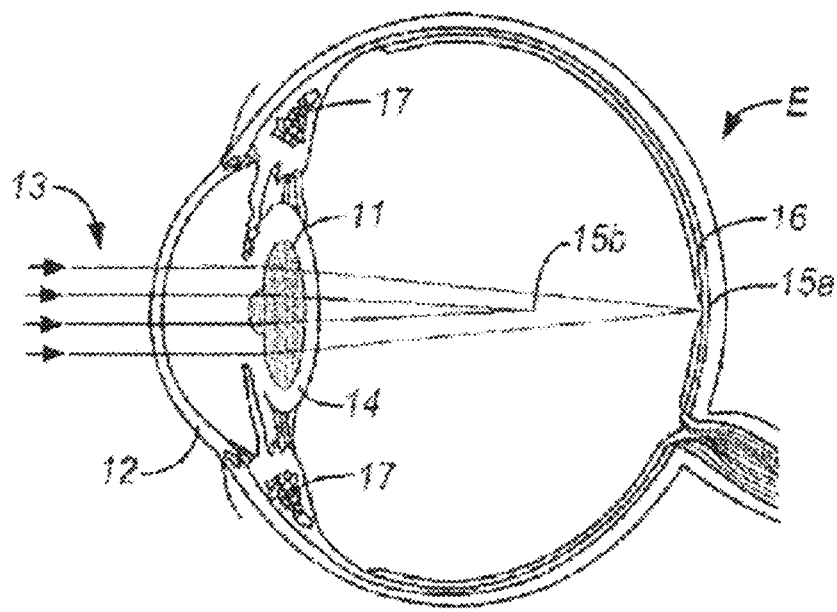
FIG. 1A illustrates a cross-sectional view of an eye with an implanted multifocal refractive intraocular lens.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference and clarity, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens. One or more support elements may be configured to secure the lens 11 to a patient's eye.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
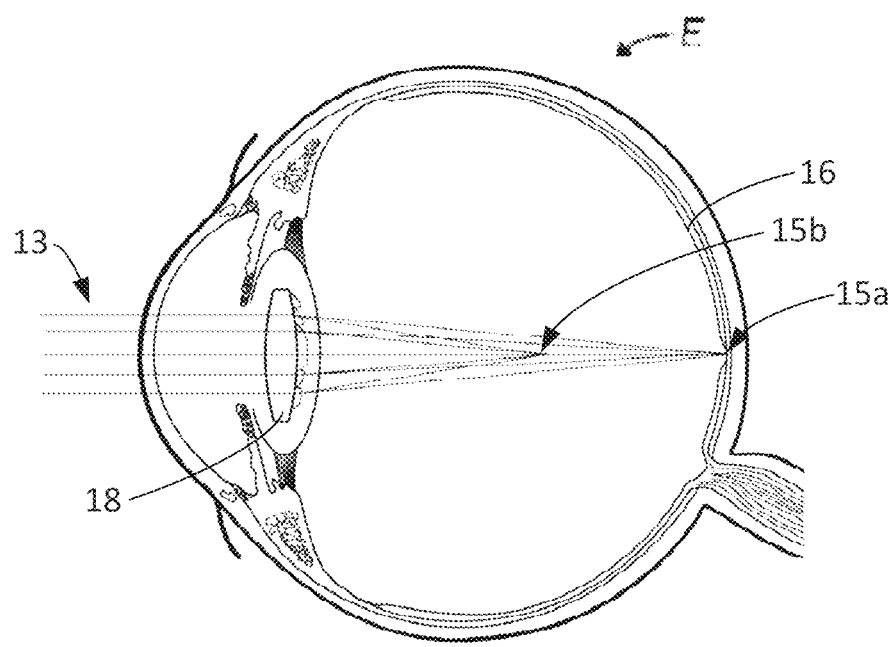
FIG. 1B illustrates a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative power, and that diffractive power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens directs incoming light into a number of diffraction orders. As light enters from the front of the eye, the multifocal lens 18 directs light to form a far field focus 15*a* on retina for viewing distant objects and a near field focus 15*b* for viewing objects close to the eye. Depending on the distance from the source of light 13, the focus on retina 16 may be the near field focus 15*b* instead. Typically, far field focus 15*a* is associated with $0^{th}$ diffractive order and near field focus 15*b* is associated with the $1^{st}$ diffractive order, although other orders may be used as well.

Bifocal ophthalmic lens 18 typically distributes the majority of light energy into two viewing orders, often with the goal of splitting imaging light energy about evenly (50%: 50%), one viewing order corresponding to far vision and one viewing order corresponding to near vision, although typically, some fraction goes to non-viewing orders.

Corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present disclosure may be applied to inlays, onlays, accommodating IOLs, pseudophakic IOLs, other forms of intraocular implants, spectacles, and even laser vision correction.

Figure 2A:
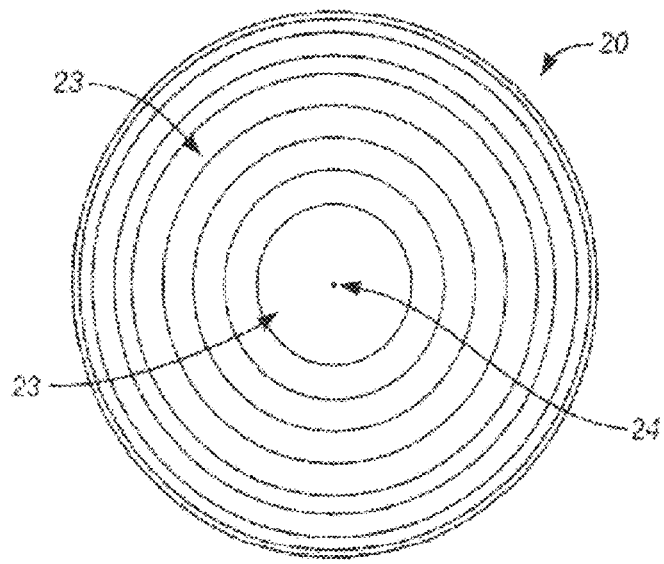
FIG. 2A illustrates a front view of a diffractive multifocal intraocular lens.
Figure 2B:
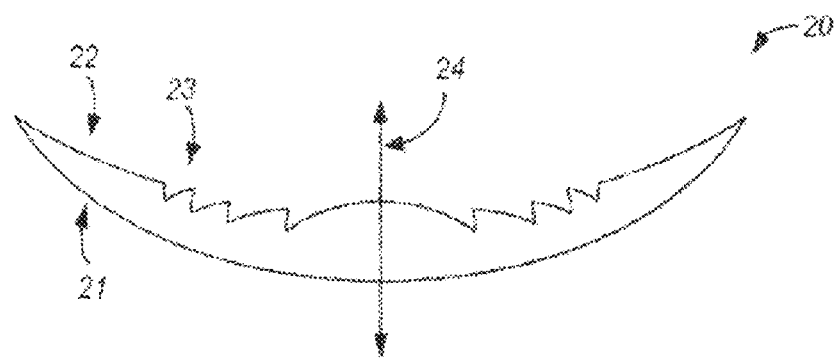
FIG. 2B illustrates a cross-sectional view of a diffractive multifocal intraocular lens.

FIGS. 2A and 2B show aspects of a conventional diffractive multifocal lens 20. Multifocal lens 20 may have certain optical properties that are generally similar to those of multifocal IOLs 11, 18 described above. Multifocal lens 20 has an anterior lens face 21 and a posterior lens face 22 disposed about optical axis 24.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a plurality of annular diffractive zones or echelettes 23 spaced about optical axis 24. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano, or other refractive surface combinations.

Conventional multifocal diffractive lenses typically provide for near and far field vision, neglecting visual performance at intermediate distances. Providing for an additional intermediate focal length by way of additional optical zones, e.g. by providing sets of at least two echelettes, can help to improve the visual performance at intermediate distances. However, as the number of optical zones increases, the risk of visual artifacts also increases. For example, in a quadrifocal diffractive lens having a near focal length, multiple intermediate focal lengths, and a far focal length; visual artifacts such as halos or glare may be visible to a user due to one or more of the boundaries between the optical zones.

Figure 3:
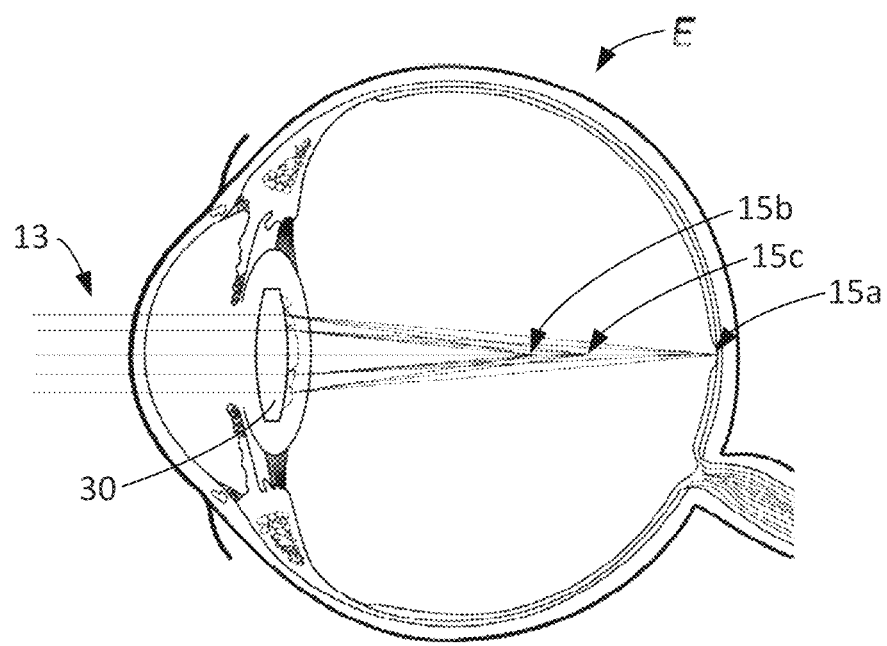
FIG. 3 illustrates a cross-sectional view of an eye having an implanted multifocal diffractive intraocular lens having an intermediate focal length.

Exemplary Multifocal Lens Shapes:

FIG. 3 shows a diffractive multifocal IOL 30 having an intermediate focal length 15*c* between near and far focal lengths 15*b*, 15*a*. The addition of an intermediate focal length 15*c* can increase the performance of the IOL 30 for users by providing improved visual acuity for viewing objects in the range of about 1.5 feet to about 5-6 feet from the eye. In general, adding a focal length can permit a presbyopic eye to focus more readily on objects at different distances.

The diffractive profile of the diffractive multifocal IOL 30 may provide for the additional focal length beyond the near focal length and far focal lengths described above by employing sets of multiple echelettes. For example, the plurality of concentric diffractive echelettes forming the diffractive profile may be split up into sets of at least two echelettes. The sets are repeating over the optic. The sets of echelettes can direct light 13 toward the near field focus 15*b* and toward the intermediate field focus 15*c*. As described above with respect to diffractive multifocal IOLs, the far focus 15*a* may typically be with a $0^{th}$ diffractive order, while the near field focus 15*b* may be associated with a $2^{nd}$ diffractive order. The intermediate focus 15*c* may be associated with the $1^{st}$ diffractive order. However, different configurations are possible. For example, a diffractive multifocal IOL may instead be configured to direct light to the far focal length 15*a* in the $1^{st}$ diffractive order, while directing light to the intermediate and near focal lengths 15*c* and 15*b* by way of $2^{nd}$ and $3^{rd}$ diffractive orders of the echelettes. In other embodiments (a quadrifocal embodiment), an additional intermediate focus (a second intermediate focus) may be provided. Greater or lesser numbers of focuses may be provided as desired in other embodiments.

Figure 4:
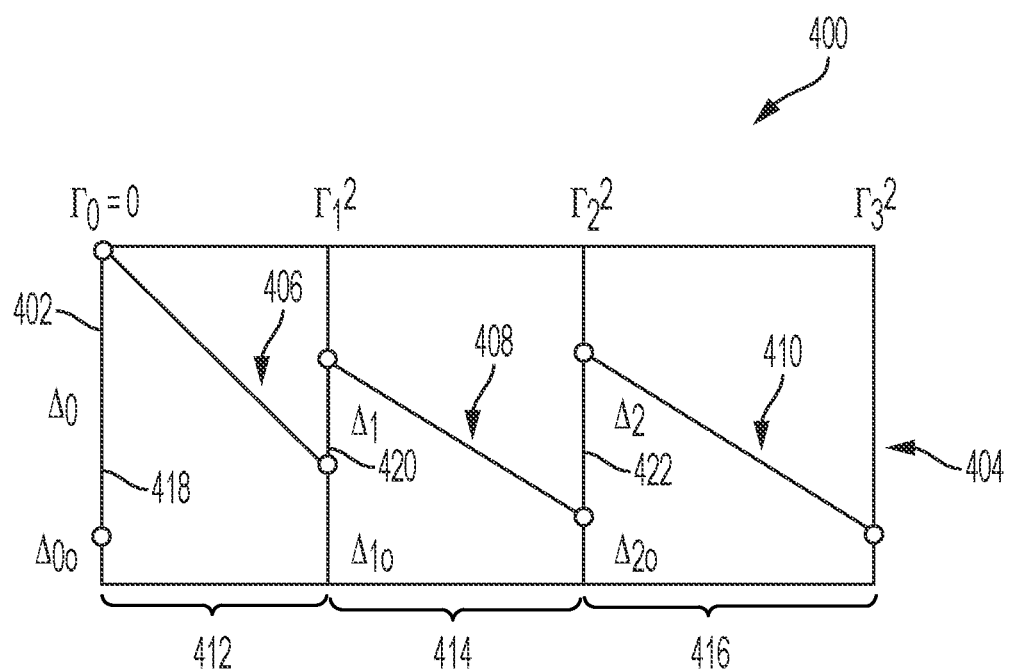
FIG. 4 is a graphical representation illustrating aspects of a conventional quadrifocal lens profile.

FIG. 4 shows a graphical representation of a portion of a parabolic diffractive profile 400, according to embodiments encompassing a set of 3 echelettes that may repeat. The figure shows the set of 3 echelettes. In the exemplary diffractive profile 400, echelettes 406, 408, and 410 are shown in the X direction (404) from a first, minimum radius $r_0$ to a maximum radius $r_3^2$. The height of the surface relief pattern (from a plane bisecting the lens) is shown in the Y direction (402) in terms of the phase shift of the echelette (or Δ), and is plotted against the square of the radial distance ($r^2$) from a central axis of the lens. The phase shift corresponds to a physical height or offset of the echelette from an underlying curve of the lens ($\Delta_o$), and may be expressed in terms of wavelength. The echelettes 406, 408, 410 are shown arranged in an A, B, C arrangement, which may be repeated. The diffractive powers of the set of echelettes is driven by the specific geometry of the echelettes, including the change in height $\Delta_1$, $\Delta_2$, over the widths of each echelette 412, 414, 416. The alternating arrangement may be referred to as a saw-tooth profile. Although only three echelettes are shown, it will be understood that any suitable number of echelettes may be positioned on a lens.

Each echelette is connected with each neighboring echelette, where present, by a transition zone. For example, the first echelette 406 connects with the second echelette 408 by a first transition zone 420; and the second echelette 408 connects with the third echelette 410 by a second transition zone 422. The transition zones 420, 422 are step heights $\Delta_1$, $\Delta_2$ from trailing edges of one echelette to leading edges of the next echelette. The first echelette 406 also transitions from a minimum height by third transition zone 418.

Figure 5:
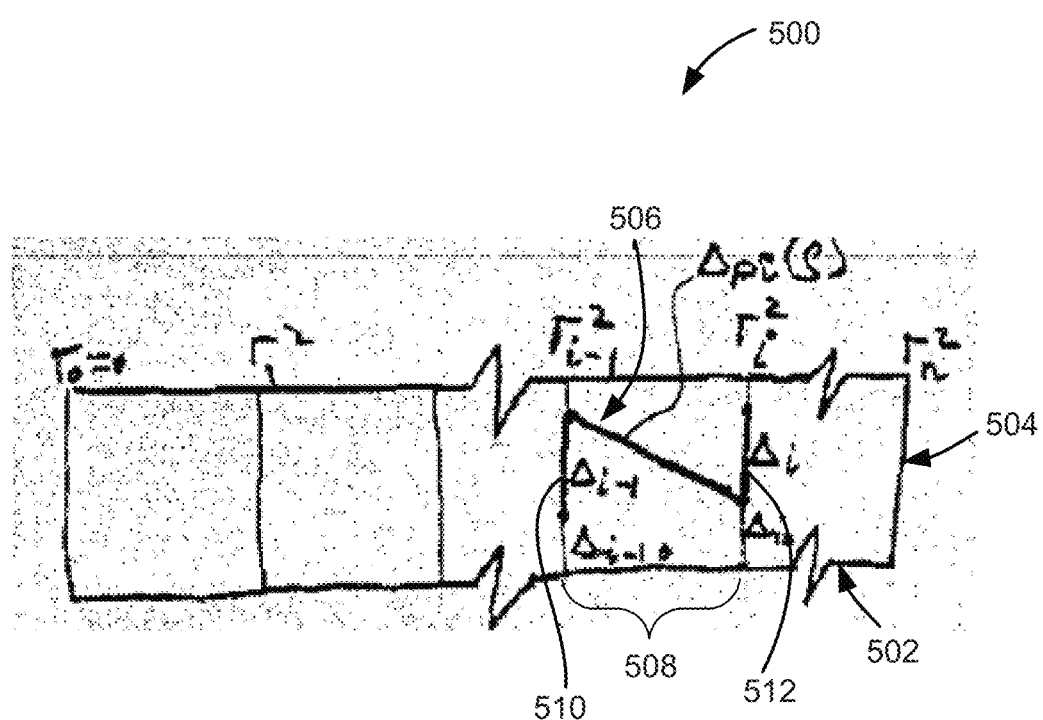
FIG. 5 is a graphical representation of a generalized multifocal lens profile.

The arrangement of the set of three echelettes 406, 408, 410 in a diffractive profile in FIG. 4 represents a general quadrifocal lens. FIG. 5, however, shows a graphical representation of a generalized set of n echelettes, representing a general profile of a multifocal diffractive lens profile 500 having n add powers, and in total n+1 powers. The profile is shown with the square of the lens radius $r^2$ (or $\rho$) on the X axis 502, and the height of the profile, or phase shift, on the Y axis (504). The diffractive powers of the set of echelettes is driven by the specific geometry of the echelettes, including the radii ($r_0, r_1, \ldots, r_i, \ldots, r_n$).

In a generalized case, where a profile height is maximum at $\rho_{i-1}$ and minimum at $\rho_i$, the initial maximum profile height 510 may be expressed as a sum of a step height $\Delta_{i-1}$ and a step offset $\Delta_{i-1o}$. The step offset is the height offset of the transition zone from the underlying base curve. The following maximum profile height 512 can be expressed as a sum of the following step height $\Delta_1$ and following step offset $\Delta_{io}$. The slope of profile $\Delta_{pi}(\rho)$ (506) can be expressed in a generalized form as follows.

$$\text{slope} = \frac{\Delta_{io} - (\Delta_{i-1} + \Delta_{i-1o})}{\rho_i - \rho_{i-1}}$$

A diffractive profile can provide for multiple focal lengths (or foci) by providing different echelette geometries in series. For example, a diffractive profile having four focal lengths, as described above, can be created by providing three different diffractive echelettes in series (forming a set of three different diffractive echelettes). The three different diffractive echelettes can be repeated, leading to repeated sets of the three different diffractive echelettes, and a diffractive profile over a portion or all of a lens surface. In conventional lenses, the diffractive profile is repeated in a saw-tooth configuration, as shown in FIG. 4.

Figure 6:
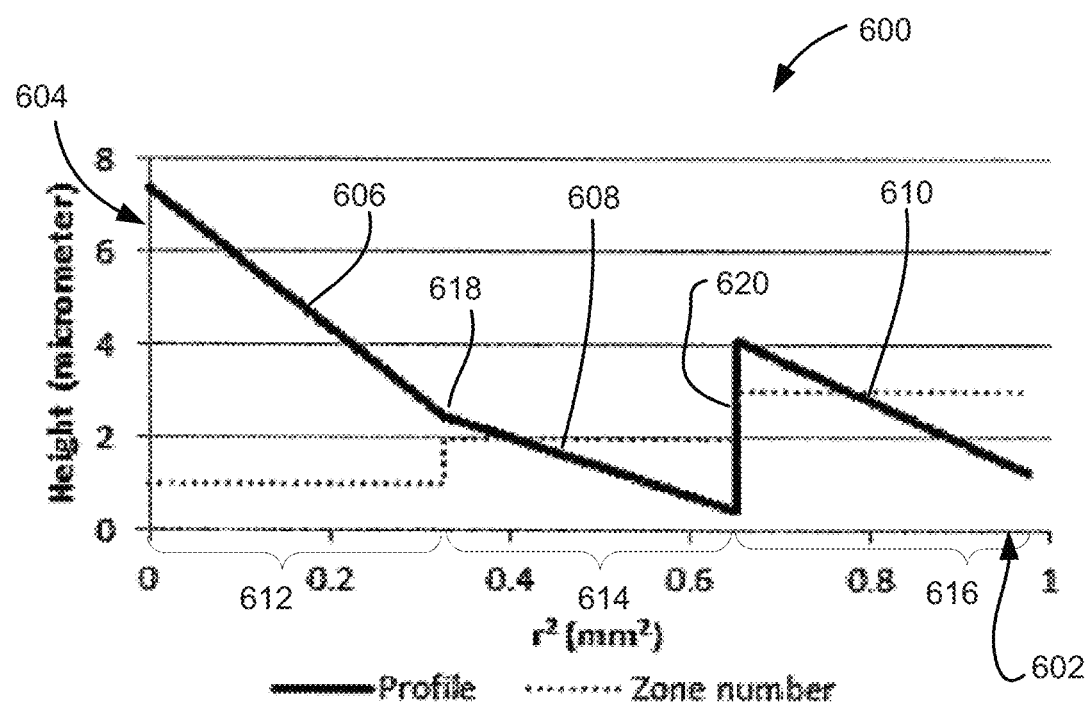
FIG. 6 is a graphical representation illustrating a quadrifocal lens profile according to certain embodiments of this disclosure.

According to certain embodiments of the present disclosure, a diffractive profile can be modified by manipulating the step heights $\Delta_i$ and following step offsets $\Delta_{io}$ between echelettes of different echelettes in a set of echelettes. For example, FIG. 6 shows a graphical representation illustrating a modified quadrifocal diffractive lens profile 600 in which a step height between two echelettes has been minimized to be essentially zero. By reducing a step height between two echelettes to zero, or about zero, the potential for that step height to generate visual artifacts such as straylight, rings, or halo can be reduced.

In the diffractive lens profile 600 of FIG. 6, the square of the radius ($r^2$ or $\rho$) is shown on the X axis 602, and the profile height ($\Delta$) is shown on the Y axis 604. The shape of the diffractive lens profile 600 is represented in relation to the square of the radius ($r^2$ or $\rho$), which is referred to as r-squared space. A first echelette 606 spans a first distance 612; a second echelette 608 spans a second distance 614, and a third echelette 610 spans a third distance 616. Notably, the transition 618 between the first and second echelette 606, 608 has been reduced to a step height of zero by matching an offset of the first echelette 606 with a maximum height of the second echelette 608. A nonzero step height 620 is still shown between the second and third echelettes 608, 610.

A typical transition zone having a nonzero step height can cause unintended redirection or concentration of light behind the lens, which may contribute to various forms of dysphotopsia. For example, nonzero step height transition zones may cause straylight, halos, glare, or other optical aberrations to appear in the far focal length. As any of the transition zones may cause such optical aberrations, reducing the number of nonzero step-height transition zones can cause a significant reduction in the incidence of such optical aberrations.

Figure 7:
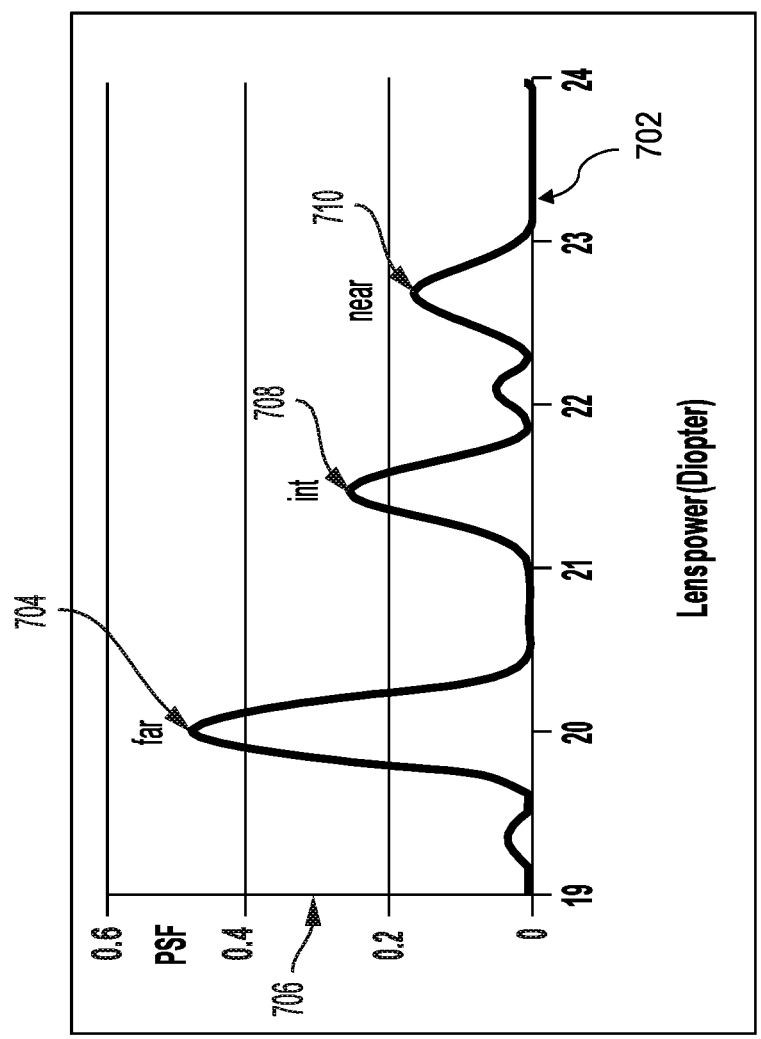
FIG. 7 is a graphical representation of a through-focus point spread function (PSF) according to certain embodiments of this disclosure.

In some embodiments, the reduction in optical aberrations may be enhanced by increasing the amount of light directed toward the far and intermediate focal lengths compared to the amount of light directed toward the near focal length. For example, a diffractive profile may be configured wherein a nonzero percentage of light is diverted to each of a near focal length, an intermediate focal length, and a far focal length, and the amount of light directed to the near focal length can be smaller than the amount directed to any other focal length. According to some embodiments, the echelettes may be arranged to direct light to the far focal length in the $0^{th}$ diffraction orders, the intermediate in the $1^{st}$ diffractive order, and the near focal length receives light via the 2nd diffractive order. In other embodiments, the echelettes may be arranged to direct light to the far focal length in the $1^{st}$ diffractive order, the intermediate focal length in the $2^{nd}$ diffractive order, and the near focal length receives light by way of the $3^{rd}$ diffractive order. In some cases, the amount of light directed to the far focal length can be greater than half of the total distribution of light that passes through the lens. The amount of light directed to the near focal length may generally be no more than 20% of the total distribution of light that passes through the lens. A through-focus point spread function (PSF) of such an embodiment is illustrated in FIG. 7. The horizontal axis 702 illustrates the total power of the lens. In this case the lens power for far vision 704 is 20 diopter. The vertical axis 706 illustrates the PSF, or light intensity. The peaks are shown for far vision 704, for intermediate vision 708, and for near vision 710. The peak for near vision 710 is the lower than the peak for intermediate vision 708, and the peak for intermediate vision 708 is lower than the peak for far vision 704. Providing a light distribution, as discussed in regard to FIG. 7, may be provided for an embodiment with a greater or lesser number of focal lengths, which may include a quadrifocal embodiment. For example, in a quadrifocal embodiment, the amount of light directed to the near focal length can be smaller than the amount directed to any other focal length. The amount of light directed to the far focal length can be greater than half of the total distribution of light that passes through the lens. The amount of light directed to the near focal length may generally be no more than 20% of the total distribution of light that passes through the lens. In these embodiments, a diffractive profile having the aforementioned light distribution may or may not include a minimized or zero step height placed between echelettes. In an embodiment with a minimized or zero step height, the minimized or zero step height may be placed between suitable echelettes, particularly between any two echelettes in a repeating set of echelettes.

Figure 8:
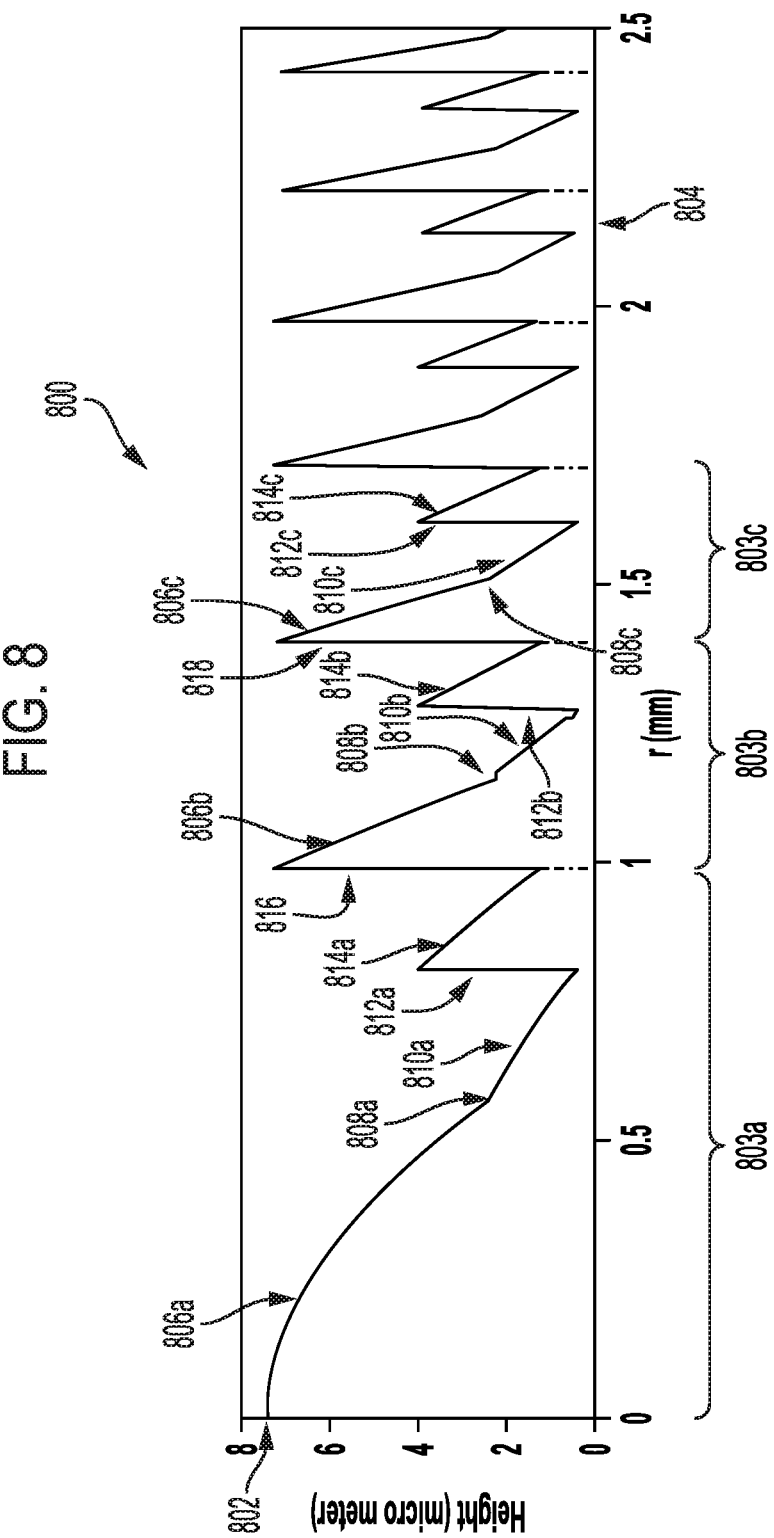
FIG. 8 illustrates a cross-sectional view of a diffractive lens surface having the quadrifocal lens profile of FIG. 6 repeated across the optic.

FIG. 8 shows a cross-sectional view of diffractive lens surface 800 having the quadrifocal lens profile that is shown in FIG. 6, but here repeated over the optic of the lens.

In the exemplary diffractive lens surface 800, the radius (r) is shown on the X axis 804 and a profile height ($\Delta$) is shown on the Y axis 802.

The diffractive lens surface 800 includes the set 803a of three echelettes 806a, 810a, 814a. The three echelettes 806a, 810a, 814a are the echelettes 606, 608, 610 shown in FIG. 6 (although shown in linear space in FIG. 8, and not in r-squared space as shown in FIG. 6). The set 803a is repeated over the optic to form repeated sets 803b, 803c, and so on, each comprising the same set defined in r²-space, configured to provide different focal lengths at respective diffractive powers. The diffractive profile accordingly includes a repetitive pattern (803a, 803b, 803c) of the echelettes repeated on the optical surface. For example, in first set 803a, a first echelette 806a, second echelette 810a, and third echelette 814a may be provided. The first echelette 806a, second echelette 810a, and third echelette 814a may each have a different profile than each other in r-squared space. The second set 803b may include a first echelette 806b, a second echelette 810b, and a third echelette 814b, each having the same profile in r-squared space as the respective first, second, and third echelettes 806a, 810a, 814a of the first set 803a. The third set 803c may include a first echelette 806c, a second echelette 810c, and a third echelette 814c, each having the same profile in r-squared space as the respective first, second, and third echelettes 806a, 810a, 814a of the first set 803a and the first, second, and third echelettes 806b, 810b, 814b of the second set 803b. The same pattern can repeat for any suitable number of sets.

The echelettes are defined in part by transition zones bounding each respective echelette. For example, regarding the first set 803a, the first echellette 806a is separated from the second echelette 810a by the first transition zone 808a; the second echelette 810a is separated from the third echelette 814a by a second transition zone 812a. The third echelette 814a is separated from the first echelette 806b of the second set 803b by the transition zone 816 between the sets 803a, 803b. Similarly, regarding the second set 803b, the first echellette 806b is separated from the second echelette 810b by the first transition zone 808b; the second echelette 810b is separated from the third echelette 814b by a second transition zone 812b. The third echelette 814b is separated from the first echelette 806c of the third set 803c by the transition zone 818 between the sets 803b, 803c. Regarding the third set 803c, the first echellette 806c is separated from the second echelette 810c by the first transition zone 808c; the second echelette 810c is separated from the third echelette 814c by a second transition zone 812c. The pattern repeats across the additional sets of echelettes.

As with conventional diffractive lenses, some of the transition zones (e.g. zones 812a, 816, 812b, 818) may have a nonzero step height. However, in accordance with embodiments, at least one pair of echelettes (e.g. zones 806a, 810a) is separated by a transition zone 808a having a step height of zero. At least one of the echelettes is connected to an adjacent echelette by a step height of zero. As the echelettes repeat across sets, further adjacent echelettes (e.g. echelettes 806b and 810b; 806c and 810c) may be separated by transition zones having step heights of zero (e.g. transition zones 808b, 808c).

Although the exact number of repeating sets shown in FIG. 8 is about six, any suitable number of repeating sets may be applied to a lens depending on the specific geometry of the echelettes and the width of the lens. For example, in certain embodiments, at least two sets repeating radially outward may be utilized. In some cases, the profile can extend over a total radius of approximately 2.5 millimeters (mm), as shown; but in other cases, the profile may extend from as little as about 1 mm to as much as about 4 mm.

Figure 9:
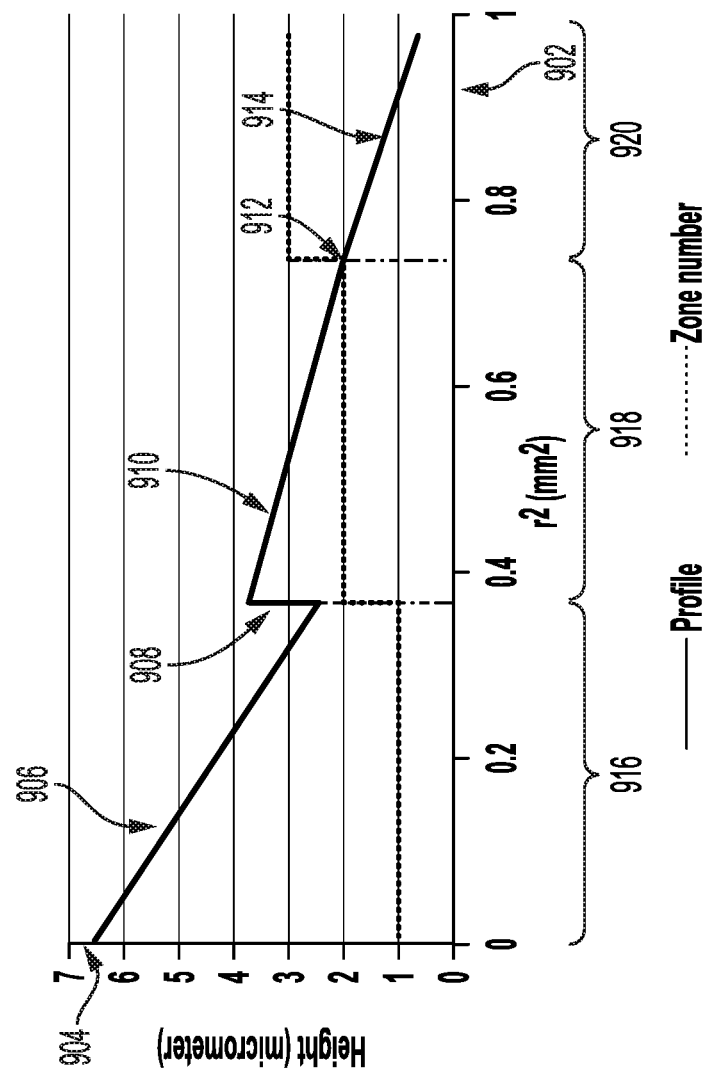
FIG. 9 is a graphical representation illustrating a quadrifocal lens profile according to certain embodiments of this disclosure.

FIG. 9 shows a graphical representation illustrating a second quadrifocal lens profile 900 according to certain embodiments of this disclosure. The quadrifocal lens profile 900 is shown in terms of profile height (or Δ), or phase shift, on the Y axis 904 against the square of the radius (or ρ) on the X axis 902 (in r-squared space). The profile 900 defines a set of three distinct echelettes 906, 910, 914 each spanning a respective portion 916, 918, 920 of the lens. In the quadrifocal lens profile 900, for an A, B, C arrangement of three distinct echelettes, the minimum or zero step height 912 is positioned at the B-C transition between the second echelette 910 and the third echelette 914. In this example, the minimum or zero step height 912 is convex, as the preceding or second echelette 910 is less steep than the subsequent or third echelette 914. A non-zero step height 908 connects the first echelette 906 to the second echelette 910.

As discussed above, the positioning of the minimized or zero step height may be adjusted. The example in FIGS. 6 and 8 shows a configuration wherein, for an A, B, C arrangement of three distinct echelettes, the minimum or zero step height is positioned at the A-B transition. The example in FIG. 9 shows a configuration wherein, for an A, B, C arrangement of three distinct diffractive zones, the minimum or zero step height is positioned at the B-C transition. The transition having minimum or zero step height is convex, as an echelette 910 merged at its respective minimum height with a steeper echelette 914. In FIG. 6, the transition having minimum or zero step height is concave, as a steeper echelette 606 merged at its respective minimum height with a less steep echelette 608.

A concave or convex transition may influence the performance of the profile, and the manufacturability. The size or extent of concave transitions may be minimized if lens is manufactured by molding. In contrast, the size or extent of convex transitions may be minimized if the lens is manufactured by lathe cutting.

Figure 10:
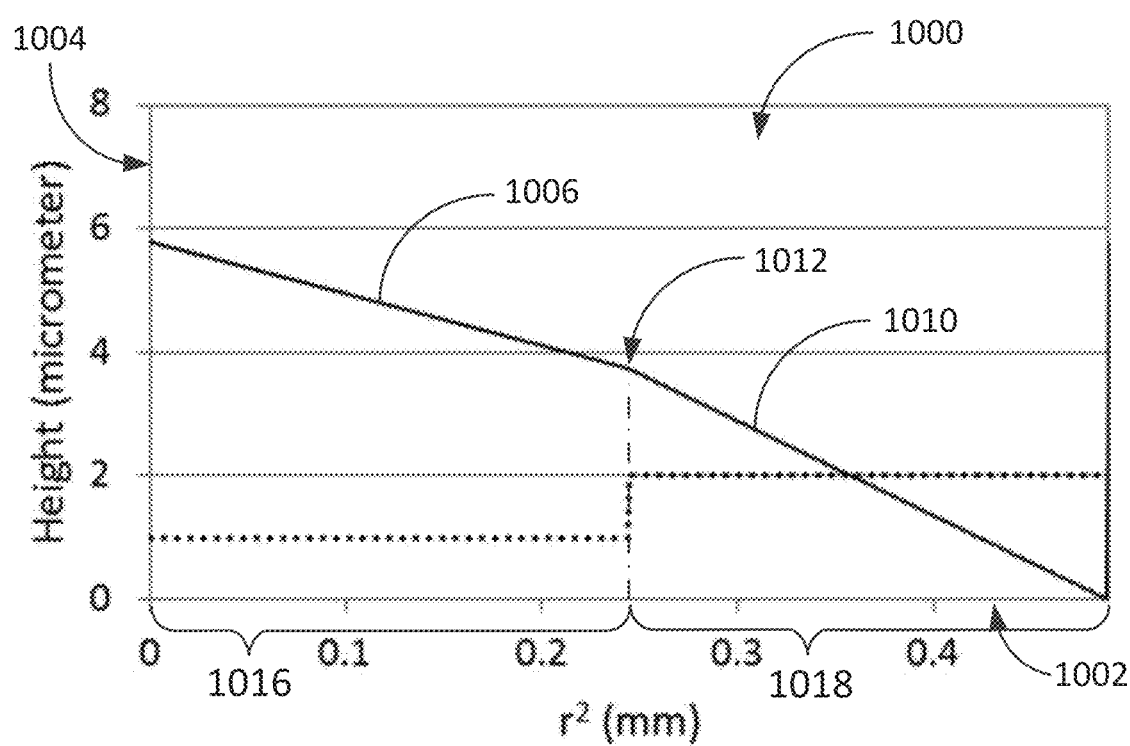
FIG. 10 is a graphical representation illustrating a trifocal lens profile according to certain embodiments of this disclosure.

FIG. 10 shows a graphical representation illustrating a trifocal lens profile 1000 according to certain embodiments of this disclosure. The trifocal lens profile 1000 is shown in terms of profile height (or Δ), or phase shift, on the Y axis 1004 against the square of the radius (or ρ) on the X axis 1002 (in r-squared space). The profile 1000 defines a set of two distinct echelettes 1006, 1010 each spanning a respective portion 1016, 1018 of the lens. In the trifocal lens profile 1000, for an A, B arrangement of two distinct echelettes, the minimum or zero step height 1012 is positioned at the A-B transition between the first echelette 1006 and the second echelette 1010. In this example, the minimum or zero step height 1012 is convex, as the preceding or first echelette 1006 is less steep than the subsequent or second echelette 1010. The set of echelettes comprising the first echelette 1006 and second echelette 1010 may be repeated over the optic of the lens for any number of repetitions, as desired.

Any of the embodiments of lens profiles discussed herein may be apodized to produce a desired result. The apodization may result in the step heights and step offsets of the repeated sets being varied according to the apodization. The sets, however, are still considered to be repeating sets over the optic of the lens.

The structures and methods discussed herein may be used to produce a lens having any number of focal lengths (monofocal, bifocal, trifocal, quadrifocal, etc.), and the diffractive profiles discussed herein may be used to produce any number of focal points (at least one focal point). The diffractive profiles may be applied to cover an annulus of the first surface or the second surface. The lens may be characterized as a monofocal lens or extended depth of focus lens.

Systems and Methods for Determining Lens Shape:

FIG. 11 is a simplified block diagram illustrating a system 1100 for generating an ophthalmic lens based on a user input.

The system 1100 includes a user input module 1102 configured to receive user input defining aspects of the user of a lens and of the lens itself. Aspects of a lens may include anatomical dimensions like pupil size performance, and lens dimensions, among other attributes, and a diffractive lens prescription, which may be a multifocal prescription. A lens prescription can include, for example, a preferred optical power or optical power profile for correcting far vision and an optical power or optical power profile for near vision. In some cases, a lens prescription can further include an optical power or optical power profile for correcting intermediate vision at two, or in some cases more than two intermediate foci, which may fall between the optical powers or ranges of optical powers described above. A pupil size performance can include a pupil radius of a patient and the visual field to be optimized. These parameters can also be related to patient's life style or profession, so that the design incorporates patient's visual needs as a function of the pupil size. Lens dimensions can include a preferred radius of the total lens, and may further include preferred thickness, or a preferred curvature of one or the other of the anterior surface and posterior surface of the lens.

A diffractive surface modeling module 1104 can receive information about the desired lens from the user input module 1102, and can determine aspects of a multizonal lens. For example, the modeling module 1104 can determine the shape of one or more echelettes of the diffractive profile of a diffractive lens, including the positioning, width, step height, and curvature needed to fulfill the prescription for each set of the echelettes, as well as the positioning of each set of echelettes. The multizonal diffractive surface modeling module 1104 can further determine the shapes of transition steps between echelettes. For example, transition steps may be smoothed or rounded to help mitigate optical aberrations caused by light passing through an abrupt transition. Such transition zone smoothing, which may be referred to as a low scatter profile, can provide for reductions in dysphotopsia by reducing the errant concentration of incident light behind the lens by the transition zones. By way of further example, echelette ordering, echelette offsets, and echelette boundaries may be adjusted to adjust the step heights between some adjacent echelettes. In particular, the multizonal diffractive surface modeling module can determine echelette offsets to set one or more step heights at echelette transitions to zero, or approximately zero, by these or similar methods.

The diffractive surface modeling module 1104 can be configured to generate performance criteria 1112, e.g. via modeling optical properties in a virtual environment. Performance criteria can include the match of the optical power profile of the multizonal lens with the desired optical power profile based on the lens prescription. The performance criteria can also include the severity of diffractive aberrations caused by lens surface. In some cases, the multizonal surface modeling module 1104 can provide a lens surface to a lens fabrication module for facilitating the production of a physical lens, which can be tested via a lens testing module 1110 for empirically determining the performance criteria 1112, so as to identify optical aberrations and imperfections not readily discerned via virtual modeling, and to permit iteration.

A refractive surface modeling module 1106 can receive information from the user input 1102 and multifocal surface modeling modules 1104 in order to determine refractive aspects of the lens. For example, provided with a multifocal prescription and a set of diffractive powers that can be generated by a diffractive profile, the refractive surface modeling module 1106 can provide a refractive geometry configured to provide a base power which, when combined with the diffractive surface, meets the requirements of the lens prescription. The refractive surface modeling module 1106 can also generate performance criteria 1112, and can contribute to providing a lens surface to a lens fabrication module 1108 for facilitating the production of the physical lens.

FIG. 12 is an example process 1200 for generating a diffractive lens surface, in accordance with embodiments. The process 1200 may be implemented in conjunction with, for example, the system 1100 shown in FIG. 11. Some or all of the process 1200 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The process 1200 includes receiving an input indicative of a diffractive lens prescription (act 1202). The input can include, e.g., a desired optical power profile for correcting impaired distance vision, a desired optical power profile for correcting impaired intermediate distance vision, a desired optical power profile for accommodating near vision, and any suitable combination of the above. Based on a desired optical power profile, a diffractive profile can be generated including a repetitive pattern of at least two echelettes (act 1204). At least one of the at least two echelettes in the repetitive pattern may be connected to an adjacent echelette by a step height of zero (act 1206).

The diffractive lens profile of the multizonal diffractive lens surface may be used in combination with a known refractive base power. To that end, a refractive lens surface may be generated having a base power that, in combination with the diffractive lens surface, meets the diffractive lens prescription (act 1208). A total lens surface can be generated based on both the refractive lens surface and the diffractive lens surface (act 1210). The refractive lens surface can include a refractive lens curvature on the anterior surface of the lens, the posterior surface of the lens, or both. Instructions can be generated to fabricate an intraocular lens based on the generated total lens surface (act 1212).

Computational Methods:

FIG. 13 is a simplified block diagram of an exemplary computing environment 1300 that may be used by systems for generating the continuous progressive lens surfaces of the present disclosure. Computer system 1322 typically includes at least one processor 1352 which may communicate with a number of peripheral devices via a bus subsystem 1354. These peripheral devices may include a storage subsystem 1356 comprising a memory subsystem 1358 and a file storage subsystem 1360, user interface input devices 1362, user interface output devices 1364, and a network interface subsystem 1366. Network interface subsystem 1366 provides an interface to outside networks 1368 and/or other devices, such as the lens fabrication module 1108 or lens testing module 1110 of FIG. 11.

User interface input devices 1362 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 1362 will often be used to download a computer executable code from a tangible storage media embodying any of the methods of the present disclosure. In general, use of the term "input device" is intended to include a variety of conventional and proprietary devices and ways to input information into computer system 1322.

User interface output devices 1364 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 1322 to a user.

Storage subsystem 1356 can store the basic programming and data constructs that provide the functionality of the various embodiments of the present disclosure. For example, a database and modules implementing the functionality of the methods of the present disclosure, as described herein, may be stored in storage subsystem 1356. These software modules are generally executed by processor 1352. In a distributed environment, the software modules may be stored on a plurality of computer systems and executed by processors of the plurality of computer systems. Storage subsystem 1356 typically comprises memory subsystem 1358 and file storage subsystem 1360. Memory subsystem 1358 typically includes a number of memories including a main random access memory (RAM) 1370 for storage of instructions and data during program execution.

Various computational methods discussed above, e.g. with respect to generating a multizonal lens surface, may be performed in conjunction with or using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

What is claimed is:

1. An ophthalmic lens, comprising:
 a first surface and a second surface disposed about an optical axis; and
 a diffractive profile imposed on one of the first surface or the second surface, wherein:
  the diffractive profile includes a repetitive pattern of at least two diffractive echelettes;
  at least one of the at least two diffractive echelettes in the repetitive pattern is connected to an adjacent diffractive echelette by a step height of zero; and
  there is no refractive region within the repetitive pattern.

2. The lens of claim 1, wherein the repetitive pattern is of three diffractive echelettes.

3. The lens of claim 2, wherein the lens is a quadrifocal lens.

4. The lens of claim 1, wherein the lens is a trifocal lens.

5. The lens of claim 1, wherein the lens is an extended depth of focus lens.

6. The lens of claim 1, wherein the lens is a monofocal lens.

7. The lens of claim 1, wherein the diffractive profile covers an area of the first surface or the second surface.

8. The lens of claim 1, wherein the diffractive profile covers an annulus of the first surface or the second surface.

9. The lens of claim 1, wherein the diffractive profile creates at least one focal point.

10. The lens of claim 9, wherein the diffractive profile creates at least two focal points.

11. The lens of claim 1, wherein the diffractive profile is operable to reduce optical aberration at the far focal length.

12. The lens of claim 1, wherein the repetitive pattern includes a form of apodization.

13. An ophthalmic lens, comprising:
 an optical surface disposed about an optical axis; and
 a diffractive profile imposed on the optical surface, wherein:
  the diffractive profile includes a set of at least two diffractive echelettes, with at least one of the at least two diffractive echelettes of the set being connected to an adjacent diffractive echelette with a step height of zero,
  the set is repeated on the optical surface, and
  there is no refractive region within the set or between adjacent repeated sets.

14. The ophthalmic lens of claim 13, wherein two of the at least two diffractive echelettes of the set have a different profile than each other in r-squared space.

15. The ophthalmic lens of claim 13, wherein the at least two diffractive echelettes of the set comprise a first diffractive echelette and a second diffractive echelette, and the step height of zero is between the first diffractive echelette and the second diffractive echelette.

16. The ophthalmic lens of claim 13, wherein the lens is a trifocal lens.

17. The ophthalmic lens of claim 13, wherein the at least two diffractive echelettes of the set comprise a first diffractive echelette, a second diffractive echelette, and a third diffractive echelette, with the second diffractive echelette positioned between the first diffractive echelette and the third diffractive echelette, and the third diffractive echelette being positioned radially outward of the second diffractive echelette, and the step height of zero is between the first diffractive echelette and the second diffractive echelette.

18. The ophthalmic lens of claim 13, wherein the at least two diffractive echelettes of the set comprise a first diffractive echelette, a second diffractive echelette, and a third diffractive echelette, with the second diffractive echelette positioned between the first diffractive echelette and the third diffractive echelette, and the third diffractive echelette being positioned radially outward of the second diffractive echelette, and the step height of zero is between the second diffractive echelette and the third diffractive echelette.

19. The ophthalmic lens of claim 13, wherein the lens is a quadrifocal lens.

20. The ophthalmic lens of claim 13, wherein the set is repeated on the optical surface radially outward from the optical axis to form at least two of the sets on the optical surface.

21. The ophthalmic lens of claim 13, wherein the set is repeated on the optical surface radially outward from the optical axis to form at least six of the sets on the optical surface.

22. The ophthalmic lens of claim 13, wherein the set is repeated on the optical surface to form a repeated set, the repeated set being apodized.

23. The lens of claim 13, wherein the lens is an extended depth of focus lens.

24. The lens of claim 13, wherein the lens is a monofocal lens.

25. A manufacturing system for making an ophthalmic lens, the system comprising:
   an input that accepts an ophthalmic lens prescription for a patient eye;
   a first module configured to generate a diffractive profile based on the ophthalmic lens prescription, wherein:
      the diffractive profile includes a repetitive pattern of at least two diffractive echelettes,
      at least one of the at least two diffractive echelettes in the repetitive pattern is connected to an adjacent diffractive echelette by a step height of zero, and
      there is no refractive region within the repetitive pattern; and
   a manufacturing assembly that fabricates the ophthalmic lens based on the diffractive profile.

26. A method of designing an intraocular lens, the method comprising:
   defining a diffractive profile including:
      a repetitive pattern of at least two diffractive echelettes, wherein at least one of the at least two diffractive echelettes in the repetitive pattern is connected to an adjacent diffractive echelette by a step height of zero, and
      wherein there is no refractive region within the repetitive pattern; and
   generating a diffractive lens surface based on the diffractive profile.

* * * * *